United States Patent
Nagata

(10) Patent No.: US 6,558,161 B2
(45) Date of Patent: May 6, 2003

(54) COMPLETELY REPRODUCIBLE ARTICULATOR

(76) Inventor: Kazuhiro Nagata, 9-37, Gakuen Nishimachi 2-chome, Kodaira-shi, Tokyo (JP), 187-0045

( * ) Notice: Subject to any disclaimer, the term of this patent is extended or adjusted under 35 U.S.C. 154(b) by 0 days.

(21) Appl. No.: 09/912,313

(22) Filed: Jul. 26, 2001

(65) Prior Publication Data

US 2002/0012896 A1 Jan. 31, 2002

(30) Foreign Application Priority Data

Jul. 28, 2000 (JP) ........................................ 2000-229120

(51) Int. Cl.$^7$ ............................................. A61C 11/00
(52) U.S. Cl. ........................................... 433/57; 433/58
(58) Field of Search ..................................... 433/57, 58

(56) References Cited

U.S. PATENT DOCUMENTS

| | | | | |
|---|---|---|---|---|
| 1,588,091 A | * | 6/1926 | Burch | 433/58 |
| 2,824,371 A | * | 2/1958 | Granger | 433/57 |
| 3,818,595 A | * | 6/1974 | Stuart | 433/57 |
| 4,260,377 A | * | 4/1981 | Hobo et al. | 433/58 |
| 4,509,919 A | * | 4/1985 | Gerbellot-Barrillon | 433/57 |
| 5,632,619 A | | 5/1997 | Polz | 433/57 |

FOREIGN PATENT DOCUMENTS

| | | |
|---|---|---|
| JP | 11-028217 | 2/1999 |
| WO | 99/58079 | 11/1999 |

* cited by examiner

Primary Examiner—John J. Wilson
(74) Attorney, Agent, or Firm—Wenderoth, Lind & Ponack, L.L.P.

(57) ABSTRACT

Disclosed is an articulator for completely reproducing mandibular movement of a living subject by performing adjustment of occlusion by regulating condylar spheres and condyle boxes disposed between maxillar and mandibular frames carrying maxillar and maxillar casts with a Bennett lift mechanism. The Bennett lift mechanism is mounted independently of the condyle boxes and on a base axis connecting the condylar spheres independently of the condyle boxes, so that vertical regulation of movements of a mandible in vertical, lateral and anteroposterior directions can be individually reproduced. Also, opening and closing movement of the maxillar and mandibular casts around the base axis (intercondylar axis) can be performed in an centric occlusion position.

20 Claims, 16 Drawing Sheets

COMPLETELY REPRODUCIBLE ARTICULATOR

BACKGROUND OF THE INVENTION

1. Field of the Invention

This invention relates to a dental articulator used for completely reproducing human jaw movement, especially articulation, in producing dental prostheses for defective or missing teeth.

2. Description of the Prior Art

Reproduction of mandibular movement is indispensable to production of dental prostheses for enabling good mastication. Interocclusal movement shows highly noticeable differences among individuals. Thus, a dental articulator capable of completely reproducing the mandibular movement of the jaw of each individual is desired, and accordingly, there have been so far proposed a variety of dental articulators for this purpose.

As one of the dental articulators, there is an arcon-type full-adjustable articulator. The arcon type denotes a structure, which is provided at its mandible portion with a condylar sphere similarly to a living subject, and at its maxilla portion with condyle path regulation. The full-adjustable articulator comprises a regulating mechanism having a function of detecting mandibular movement in a form of three-dimensional movement of the jaw to effect three-dimensional regulation for the entire movement.

In Japanese Patent No. 2866084 (Japanese Patent Application Publication No. HEI 11-028217), the inventors of the present invention disclosed an arcon-type "completely reproducible articulator" capable of perfect reproduction of mandibular movement. The articulator disclosed in this Japanese publication will be discussed, upon explaining an ordinary technique in relation to the articulator.

First, terminology for describing an occlusion will be briefly defined. In dentistry, the front, side and plane in a general sense are expressed in terms of "frontal plane", "sagittal plane" and "occlusal plane", respectively. In general, the side toward which mandibular movement is directed is termed the "working side", and the opposite side is termed the "balancing side" or "non-working side". Of the maxilla and mandible, which constitute the jaw, the mandible is movable and restrained in movement via configuration of the glenoid fossae accommodating right and left "condyle heads". The mandible moves in five directions, i.e. protrusive, lateral (leftward), lateral (rightward), posterior and vertical directions. A center of a condylar point is termed "condylar point", a line connecting centers of right and left condyle heads is termed "condylar axis", and locus along which the condylar point moves along the glenoid fossae is termed "condyle path".

The conventional full-adjustable articulators also have various types of contrivances for reproducing the mandibular movement, which are common in principle.

First, jaw movement to be reproduced is fulfilled by the mandibular movement made in the five directions as touched upon above. However, all five-directional mandibular movements, may be practically ruled out of the movements of the conventional articulators. That is, movement of the condylar points in the protrusive, leftward and rightward directions will suffice for reproducing the jaw movement. With respect to the lateral movement of the jaws, when the mandible moves rightward, the right condyle head works as the working side and the left condyle head works as the balancing side. The reverse is also true when the mandible moves Leftward. Thus, the jaw movement to be reproduced must vary according to the movement of each condyle head, which is performed in different manner in moving the mandible rightward or leftward.

That is to say, the jaw movement at the time of the protrusive motion of the condyle heads and the lateral motions of the right and left condyle heads when the respective condyle heads work as the working side or balancing side may be accurately reproduced. In other words, it may be required to reproduce only the protrusive movements of the right and left condyle heads and the lateral movements of the condyle head (working condyle head) and condyle head (balancing condyle head).

There has been a method for reproducing movement of the condyle heads noted above, in which a three-dimensional reproduction of the movement is effected by combining movements of the jaw in an internal-external, upward-downward and anteroposterior directions. With a dental articulator, jaw movement has been recognized by bringing a plate member called a "regulation plate" in touch with the condyle heads so as to permit the condyle heads to move along the regulation plate, and varying an angle (gradient) of the regulation plate to derive a direction in which the regulation plate moves relative to condyle heads. Hence, internal-external, upward-downward and anteroposterior regulation plates are provided for each condyle head in order to regulate movements of the condyle head, so that the condyle heads are guided in composite directions in which the regulation plates are regulated.

In a common articulator, a vertical regulation plate is called a "sagittal condylar path inclination plate", a mesio-lateral regulation plate is called a "Bennett plate", and an anteroposterior regulation plate is called a "rear wall".

Next, a regulating method will be described in detail. At the time of protrusive movement of a jaw, both condyle heads move in an anterior-downward direction during the protrusive movement, thereby to be restrained in a vertical direction. During lateral movement of the jaw, the working condyle head moves slightly, but the balancing condyle head largely moves inwardly in an anterior-downward direction. Consequently, the balancing condyle head is restrained in vertical and lateral directions, and simultaneously, the working condyle head is restrained in vertical and anteroposterior directions, while being thrust outwardly.

What does matter at this point is usage of vertical regulation for reproducing three sets of vertical components of the protrusive movement, right lateral movement and left lateral movement. To be specific, the sagittal condylar path inclination plate used for vertical regulation corresponds to these movements made in three directions, but the vertical components of the movements in the three directions varies relative to each other with the direction in which the jaw moves. Thus, in a case that the mandible is regulated in its right lateral movement and successively in its left lateral movement, the right condyle head first works as the working condyle and successively as the balancing condyle. At that time, it is necessary to readjust an angle of the sagittal condylar path inclination plate. Therefore, work required for the regulation disadvantageously requires much time and labor and proves to be troublesome.

To overcome the unfavorable problems described above, there has been adopted a method in which a rotary inclination mechanism called a "Fischer slide" is attached to the sagittal condylar path inclination plate. FIG. 15 shows a conventional articulator adopting a method using a "Fischer slide". As shown in FIG. 15, one sagittal condylar path inclination plate 522 is provided with an inclination rotatable about an intercondylar axis (A) and an inclination (of the Fischer slide) rotatable about a sagittal condylar path inclination axis (C), thereby to possess two inclination angles, so that the sagittal condylar path inclination plate 522 can be restrained in two directions of vertical movement with one regulation plate. However, this conventional method capable of reproducing only two of the movements made in three directions required for vertical regulation could not completely reproduce the desired mandibular movement. In FIG. 15, reference numeral 513 denotes the condyle head, 521 denotes the Bennett plate (angular regulation plate rotatable about the axis B), and 523 denotes the rear wall (angular regulation plate rotatable about the axis R).

To overcome the disadvantage suffered by the conventional articulator, the inventor of this invention proposed in Japanese Patent No. 2866084 an improved articulator capable of completely reproducing the mandibular movement.

To be more specific, a "Bennett lift mechanism" disclosed in Japanese Patent No. 2866084 enables vertical regulation of the working condyle, and consequently enables three directional movements of the condyle heads. The Bennett lift mechanism was invented by the inventor of this invention and is explained in detail in Japanese Patent No. 2866084.

Operation of the articulator disclosed in Japanese Patent No. 2866084 is schematically illustrated in FIG. 16. As illustrated, a proposed articulator $1m$ has a structure for reproducing jaw movement made with moving the maxilla. A base $102m$ is provided on a mandibular frame $10m$ for a mandibular cast 2, and is provided at both its side ends with condylar sphere members $13m$ in imitation of the condyle heads. A condyle box $14m$ constituted by a plurality of regulation plates is brought into contact with the condylar sphere members $13m$, so that a maxillar frame $11m$ for supporting a maxillar cast 3 is guided through the condyle box $14m$. Therefore, rightward movement of the mandibular cast is fulfilled by moving the maxillar cast leftward, and leftward movement of the mandibular cast is fulfilled by moving the maxillar cast rightward. Thus, relative movement of the mandible and maxilla can be reproduced in this manner.

The proposed articulator $1m$ is provided with a Bennett lift mechanism $15m$ independent of the condyle box $14m$, in such a state that a cam $50m$ formed on a rear of the base $102m$ comes into contact with a pin $51m$.

The aforementioned Bennett lift mechanism $15m$ of the proposed articulator is used exclusively for regulating vertical movement of the working condylar sphere member $13m$. That is, the Bennett lift mechanism $15m$ on the working side is operated when the balancing condylar sphere member $13m$ moves inwardly in an anterior-downward direction by virtue of the vertical regulation plate (sagittal condylar path inclination plate) and the mesio-lateral regulation plate (Bennett plate). At this time, the working condylar sphere member $13m$ is apart from the sagittal condylar path inclination plate, and simultaneously, restrained in vertical movement by the Bennett lift mechanism $15m$. The sagittal condylar path inclination plate contributes not only to protrusive movement of the condylar sphere member, but also to lateral movement of the balancing condylar sphere member $13m$, and consequently restrains the forward and balancing movements of the condylar sphere members through agency of the Fischer slide.

Accordingly, the articulator $1m$ makes it possible to reproduce all jaw movements in protrusive, balancing and working states, which require vertical restriction in movement, in addition to the Bennett lift mechanism $15m$.

However, the Bennett lift mechanism $15m$ disclosed in Japanese Patent No. 2866084 (hereinafter referred to as a "prior art Bennett lift mechanism") has disadvantageously entailed a problem such as a possible malfunction of the maxillar cast 3 and mandibular cast 2 at a time of opening and closing.

This is attributable to the cam $50m$ formed on the rear of the base $102m$ colliding with the pin 51 mounted on the maxillar frame in opening or closing the maxillar cast 3 and mandibular cast 2, which consequently causes deviation of a rotating axis of the opening and closing movements from an intercondylar axis toward the rear of the base $102m$. Although a line (intercondylar axis) connecting the right and left condyle heads should serve as a rotational center, it is shifted to a line connecting right and left Bennett lift mechanisms $15m$ in practice. As a result, rotation is made about an axis carrying fulcrum $52m$ at which the pin 51 comes into contact with the cam $50m$, and consequently detaches the condylar sphere $13m$ from the condyle box $14m$. Besides, since the pin $51m$ of the Bennett lift mechanism $15m$ comes into contact with an upper surface of the cam $50m$, the fulcrum $52m$ is slid on the surface when opening the maxillar and mandibular casts, and consequently causes further deviation of the rotational axis. As a result, the maxillar cast and mandibular cast disadvantageously get out of position and lack stability. The work of confirming occlusion when opening and closing the maxillar and mandibular casts is of great importance from the point of view of usage of the articulator. In spite of the needs for high reliability and reproducibility of the articulator, the proposed articulator has suffered a disadvantage in that deviation of a central axis as noted above renders the articulator considerably inconvenient to operate.

The proposed articulator is further disadvantageous in that there is a structural limit in the angle at which the regulation plates of the condyle box $14m$ are restrained. That is, the regulation plates such as the sagittal condylar path inclination plate, Bennett plate and rear wall, which constitute the condyle box $14m$, collide with one another when they change in gradient, and thus restrain angular movements of the regulation plates.

OBJECT OF THE INVENTION

An object of the present invention is to provide an articulator capable of completely and faithfully reproducing movements of a mandibular cast and maxillar cast by analogy of occlusion of a human.

Another object of the present invention is to provide an articulator capable of tight and rigid hinge movement in opening and closing the maxillar and mandibular casts in a centric occlusion position.

Still another object of the present invention is to provide an articulator capable of lightening restraint on angular movements of regulation plates, which is possibly caused by collision of the regulation plates.

SUMMARY OF THE INVENTION

To attain the objects described above according to the present invention, there is provided a completely reproducible articulator comprising a maxillar frame for supporting a maxillar cast, a mandibular frame for supporting a mandibular cast, a pair of condylar spheres placed between the mandibular and maxillar casts, condyle boxes placed between the mandibular and maxillar casts, and Bennett lift mechanisms disposed on a base axis connecting the condylar spheres independent of the condyle boxes.

The mandibular and maxillar casts are movable laterally. During lateral movement of the mandibular and maxillar casts, one of the condylar spheres serves as a working condylar sphere, and the other serves as a balancing condylar sphere. With the Bennett lift mechanisms, the working condylar sphere is independently restrained in its vertical movement during lateral movement of the mandibular and maxillar casts. The Bennett lift mechanisms disposed on the base axis (equivalent to the condylar axis) rotate about the base axis when opening and closing the mandibular and maxillar casts in a centric occlusion position.

There may further be disposed a pair of second condylar spheres on the base axis, so that vertical movement thereof can be restrained by the Bennett lift mechanisms, thus reproducing movements of the working side condyle.

An axis fixing mechanism may be provided for coinciding the rotational center with the base axis while opening and closing the mandibular and maxillar casts in the centric occlusion position, thus to overcome instability in which the mandibular and maxillar casts are easy to separate. Accordingly, the opening and closing of the mandibular and maxillar casts can be stably performed repeatedly while retaining the rotational axis on the base axis, to consequently improve reliability in operation.

The axis fixing mechanism may be provided with an engaging member for elastically connecting the mandibular frame and the maxillar frame, so that the mandibular and maxillar casts are caught with this engaging member so as to be prevented from being separated. As a result, reliable opening and closing movements about the base axis can be performed.

Or, the axis fixing mechanism may be provided with an axial rod and an engaging portion for elastically connecting the mandibular cast and the maxillar cast, so that the mandibular and maxillar casts are caught by the axial rod and engaging portion so as to be prevented from being separated from each other. As a result, the reliable opening and closing movements about the base axis can be performed.

Independent of the condyle box, anteroposterior regulation plates may be disposed for regulating movement in the anteroposterior direction relative to the working condylar sphere, so as to be prevented from colliding with each other in the condyle box. As a result, limits in which the regulation plates are movable can be made large.

Or, inner and outer regulation plates for regulating lateral movement of the working condylar sphere may be disposed independent of the condyle box, so as to be prevented from colliding with each other in the condyle box. As a result, limits in which the regulation plates are movable can be made large.

Other and further objects of this invention will become obvious upon an understanding of the illustrative embodiments about to be described, or will be indicated in the appended claims, and various advantages not referred to herein will occur to one skilled in the art upon employment of the invention in practice.

DESCRIPTION OF THE PREFERRED EMBODIMENTS

Figure 1:
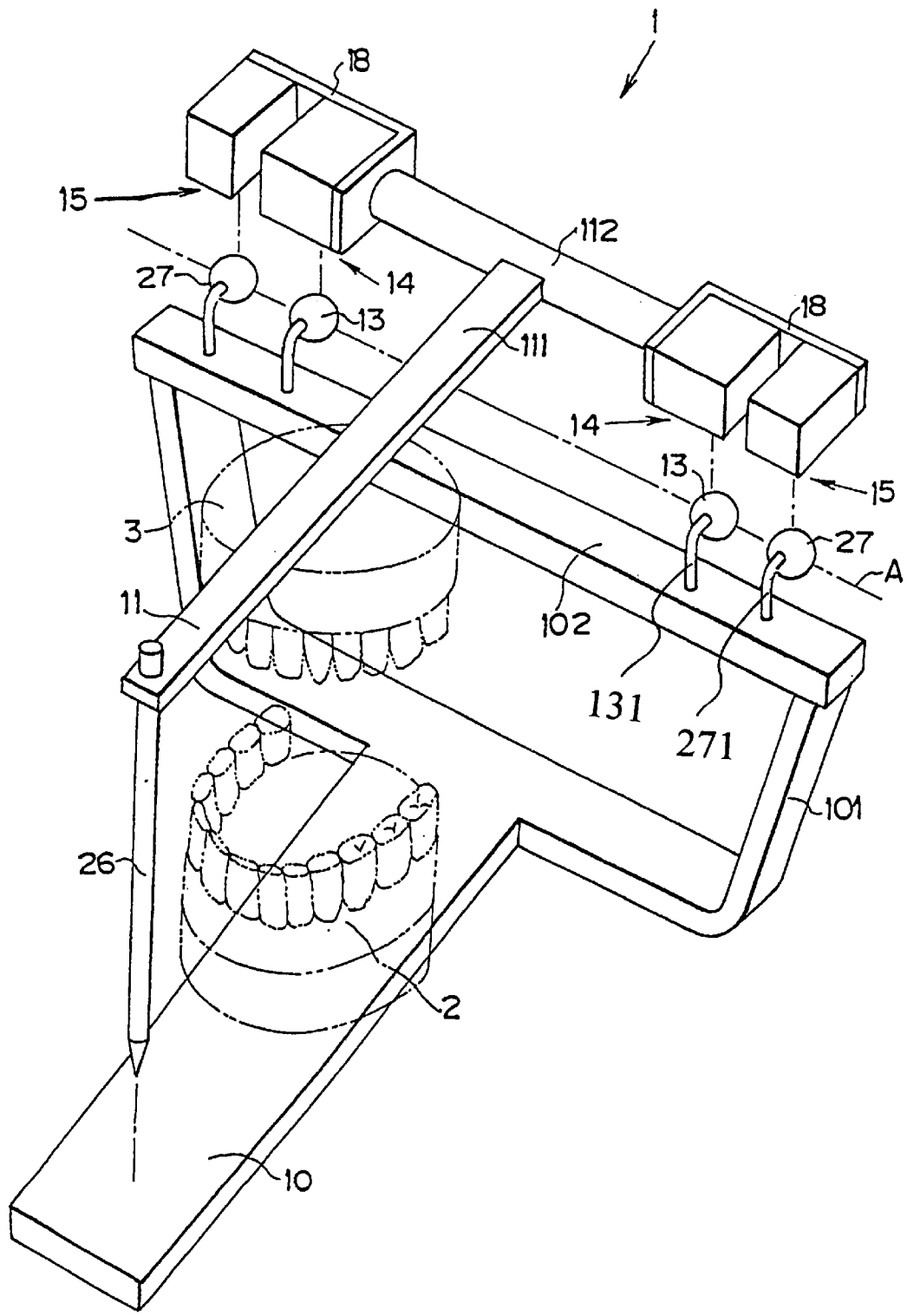
FIG. 1 is a perspective view schematically illustrating a basic structure of a first embodiment of an articulator according to the present invention.
Figure 2:
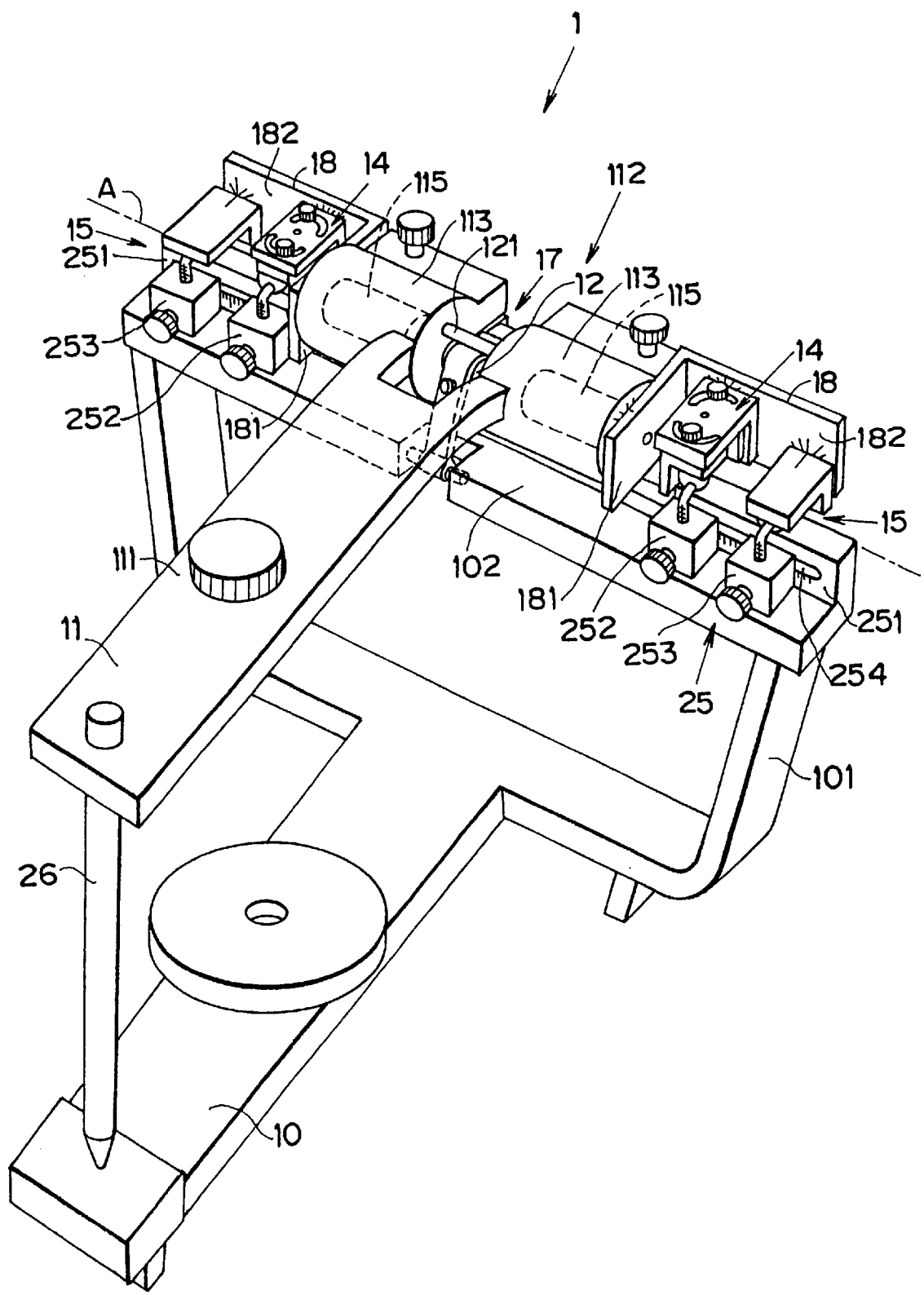
FIG. 2 is a perspective view schematically illustrating the articulator of the invention.

As illustrated in FIGS. 1 and 2 as a first embodiment of the present invention, an articulator 1 of the invention comprises a maxillar frame 11 for supporting a maxillar cast 3, a mandibular frame 10 for supporting a mandibular cast 2, a pair of condylar spheres 13 placed between the mandibular and maxillar frames 10 and 11, condyle boxes 14 in contact with the condylar spheres, and Bennett lift mechanisms 15 which are disposed on a base axis A and are in contact with second condylar spheres 27 independently of the condyle boxes 14.

The articulator 1 in this embodiment is an arcon-type full-adjustable articulator, in which the condyle boxes 14 are disposed on the maxillar frame 11 and come in contact with the condylar spheres 13 of the mandibular frame 10. In this structure, the base axis A corresponds to an intercondylar axis of a living person. By adjusting the maxillar frame 11 in accordance with a regulating surface of the condyle box 14, movement of the mandible relative to the maxilla of the living person can be reproduced.

The Bennett lift mechanisms 15 serve to regulate vertical movement of second condylar spheres 27 disposed on the base axis A. Thus, the Bennett lift mechanisms in this invention can work on the base axis A, dissimilarly to a conventional articulator. The second condylar spheres 27 are disposed as a pair on the mandibular frame in the vicinity of the condylar spheres 13, and correspondingly, the Bennett lift mechanisms 15 are provided as a pair. In the illustrated embodiment, the second condylar spheres 27 are placed outside the condylar spheres 13.

Between the maxillar frame 11 and mandibular frame 10, there is provided an axis fixing mechanism 17 for coinciding a rotational center of an opening with the base axis A while opening and closing the mandibular cast 2 and maxillar cast 3 in a centric occlusion position thereof.

The maxillar frame 11 is provided with a mounting member 111 for mounting the maxillar cast 3, a base member 112, and condyle members 18 for mounting the condyle boxes 14 and Bennett lift mechanisms 15 on both ends of the base member 112.

The base member 112 comprises a central shaft 12, holding members 113 for holding both end portions of the central shaft 12, cylinders 115 supported by the holding members 113 in a retractable manner on opposite sides of the central shaft 12, and a movement regulating shaft 121 disposed in parallel with the central shaft 12. The cylinders 115 are retractable into the holding members 113 to allow a length of the base member 112 to vary. The central shaft 12 and the cylinders 115 are coaxially assembled coinciding with the base axis A in the centric occlusion position, to place the maxillar frame 11 on the mandibular frame 10 in position. At a free end portion of the mounting member 111, there is mounted an incisal guide pin 26 for regulating a downward movement of the maxillar frame 11. The incisal guide pin 26 is adjustable in its length.

Each condyle member 18 assumes a substantially L-shape, and has a side plate 181 mounted on an end surface 116 of a respective cylinder 115. On another side plate 182 of each condyle member 18, a supporting member 19 of condyle box 14 and a Bennett lift member 28 of Bennett lift mechanism 15 are rotatably mounted.

On a model of a jaw of a human being, one pair of condylar spheres 13 is provided and mounted in the vicinity of each end portion of a base 102 disposed on leg members 101 of the mandibular frame 10.

Each condylar sphere 13 is supported by a rod 131 on the base axis A. Since the rod 131 is nothing but a supporter for the condylar sphere 13, it is desired to be formed and positioned so as not to prevent the maxillar frame 11 from moving during the opening and closing operation. The rod 131 is extended rearwardly upwardly at an angle θ (45° in the illustrated embodiment).

The second condylar spheres 27 are disposed as a pair on the base 102 outside the condylar spheres 13. The second condylar spheres 27 in the articulator of the invention are not found in a living body, but serve to independently regulate vertical movement of the condylar spheres 13 by using the Bennett lift mechanism 15.

Each of the second condylar spheres 27 is supported by the rod 271 similar to the condylar spheres 13 on the base axis A. Similarly to the rod 131, the rod 271 is also extended rearwardly upwardly at an angle θ (45° in the illustrated embodiment).

Each condylar sphere 13 and each second condylar sphere 27 are mounted on the base 102 through an intercondylar adjusting mechanism 25. The intercondylar adjusting mechanism 25 has functions of positioning the condylar sphere 13 and the second condylar sphere 27 on the base 102, adjusting intervals between the condylar spheres 13 and the second condylar spheres 27, and adjusting heights of the condylar spheres 13 and the second condylar spheres 27.

Each intercondylar adjusting mechanism 25 comprises moving members 252 and 253 on which a condylar sphere 13 and a second condylar sphere 27 are mounted so as to adjust the heights of the condylar sphere 13 and the second condylar sphere 27, and fixing member 251 mounted on the base 102 for supporting the moving members 252 and 253 in a horizontally movable state. Circumferences of a slit 254 in the fixing member 251 and the rods 131 and 271 are calibrated so as to facilitate confirmation of adjusted positions of these components.

Figure 3:
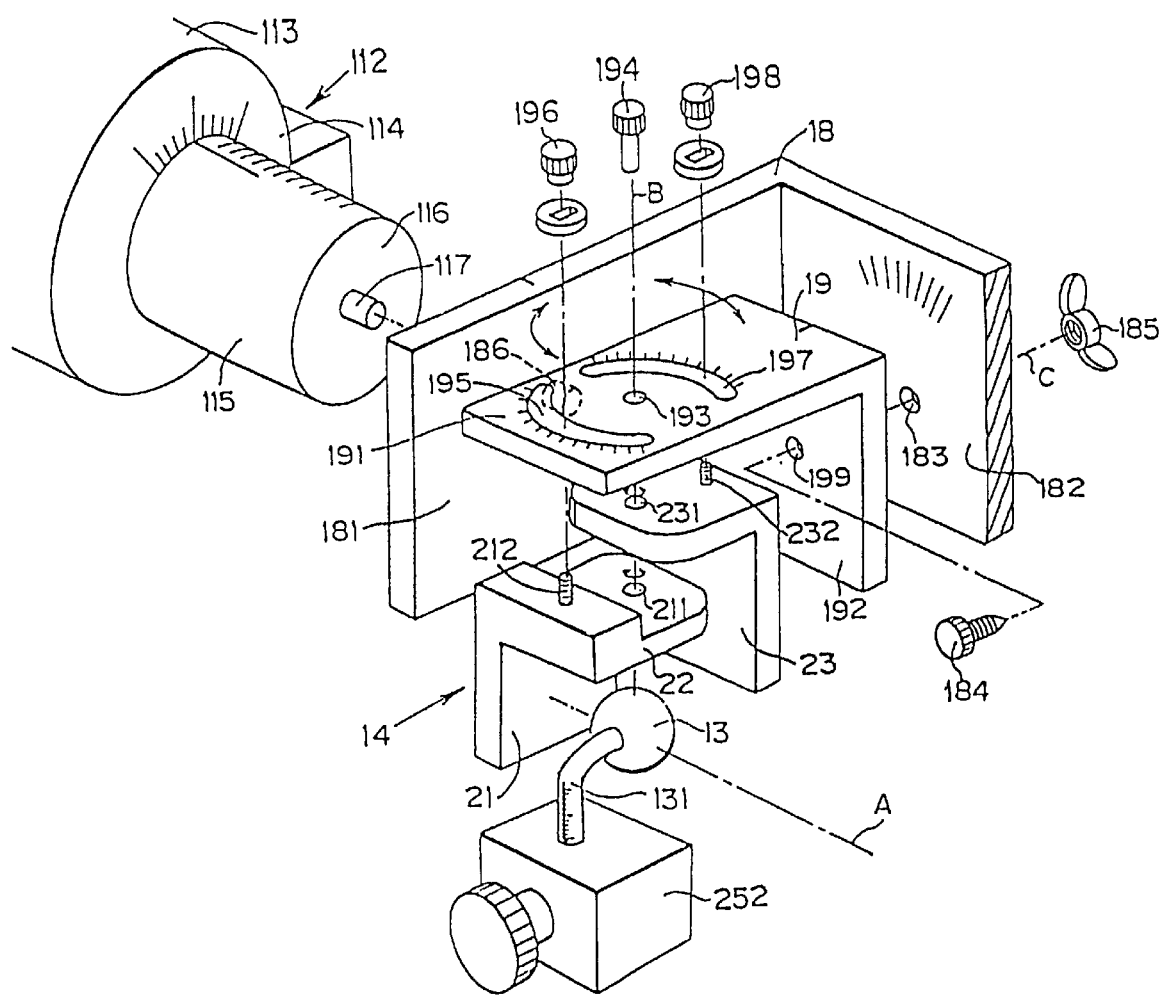
FIG. 3 is an exploded perspective view illustrating a condyle box in the articulator of the invention.

As shown in FIG. 3, the condyle box 14 coming in contact with the condylar sphere 13 has a side plate 181 with a hole 186 into which a shaft 117 of the cylinder 115 is inserted and secured by use of suitable structure. The end face 114 of the holding member 113 is also calibrated so as to facilitate confirmation of a rotational angle of the condyle box 14. The holding member 113 and the cylinder 115 are slidably connected. An outer peripheral surface of the cylinder 115 is also calibrated so as to facilitate confirmation of an adjusted condition of the cylinder.

In the other side plate 182 of the condyle member 18, there is bored a hole 183 for supporting the condyle box 14 in a freely rotatable state. The condyle box 14 is provided with a support member 19 and a plurality of regulation plates, which will be described below. The regulation plates are rotatably mounted on the support member 19, so as to move while being in contact with the condylar sphere 13, consequently to guide the maxillar frame 11 in motion.

The regulation plates are formed of a Bennett angle regulation plate 21 for regulating a Bennett angle when the relevant condylar sphere 13 coming in contact with the regulating plate works as a balancing part, a sagittal condylar path inclination plate 22 for regulating a sagittal condylar path inclination, which is united to the Bennett angle regulation plate 21, and a rear wall 23 for regulating movement in an anteroposterior direction when the relevant condylar sphere 13 works as a working part. That is, the Bennett angle regulation plate 21 is a mesio-lateral regulation plate, the sagittal condylar path inclination plate 22 is a vertical regulation plate, and the rear wall 23 is an anteroposterior regulation plate.

The support member 19 is formed of an upper plate 191 and a side plate 192 arranged in a substantially L shape. The support member 19 and the Bennett angle regulation plate 21 are rotatably united by thrusting a screw 194 into a hole 193 formed in the upper plate 191, a hole 231 formed in an upper surface of the rear wall 23 and a hole 211 formed in an upper surface of the Bennett angle regulation plate 21.

The Bennett angle regulation plate 21 is supported rotatably about an axis B by the support member 19 and retained by a screw 196 in such a state that a columnar member 212 projecting from the upper surface of the Bennett angle regulation plate 21 is fitted into a crescent slit 195 formed in an upper surface of the upper plate 191, so as to be adjusted to a desired angle. This angle can readily be confirmed by finding graduations formed in an edge portion of the slit 195.

Similarly, the rear wall 23 is supported rotatably about the axis B by the support member 19 and retained by a screw 198 in such a state that a column member 232 projecting from the upper surface of the rear wall 23 is fitted into another crescent slit 197 formed in the upper surface of the upper plate 191, so as to be adjusted to a desired angle. This angle of the rear wall 23 can readily be confirmed by finding graduations formed in an edge portion of the slit 197.

It is desirable to form the slit 197 so as to allow the rear wall 23 to move to a position at which the rear wall is parallel to the side panel 181 of the condyle member 18. This is because posterior movement of the mandible of the living body is possibly necessary according to a clinical case. In the case of reproducing the posterior movement of the mandibular cast of the articulator 1, the shape of the slit 197 may be so designed that the movement of the rear wall 23 can be controlled to temporarily release restraint in an anteroposterior direction of the rear wall 23.

The support member 19 is united rotatably about an axis C to the side panel 182 of the condyle member 18 by a screw 184 inserted through a hole 199 formed in the side panel 192 of the support member 19 and a hole 183 formed in the side panel 182 of the condyle member 18, and tightened by a wing nut 185. The support member 19, plate 22 and screw 184 constitute a lift mechanism. By turning the support member 19 about the axis C, the sagittal condylar path inclination plate 22 can be manipulated so as to reproduce a desired Fischer angle. The side panel 182 is calibrated so as to facilitate confirmation of an adjusted angle of the sagittal condylar path inclination plate 22.

Figure 4:
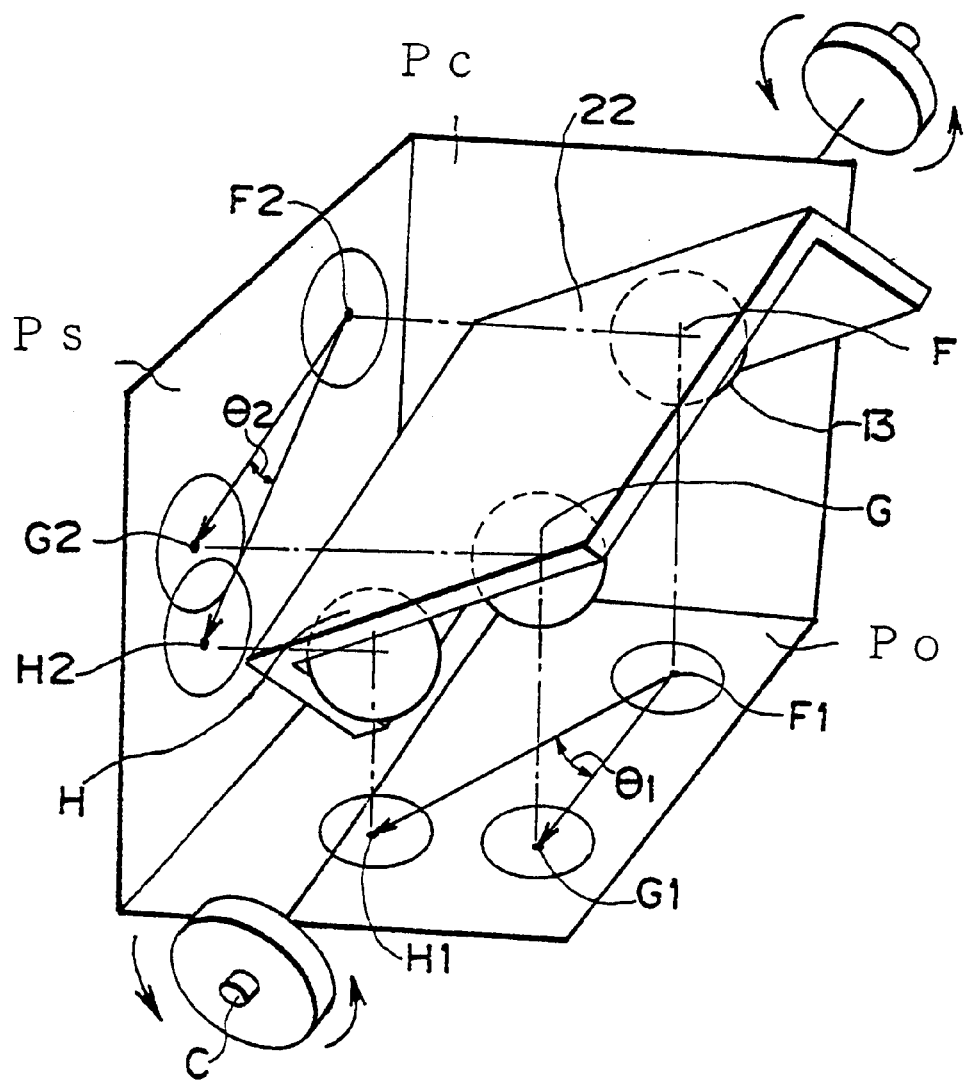
FIG. 4 is an explanatory diagram showing movement of a condylar sphere in the articulator of the invention.

Next, movement of the condylar sphere 13, which is restrained in movement within the condyle box 14 having the aforementioned structure, will be explained with reference to FIG. 4. A left temporomandibular joint (rightjoint in FIG. 2) or the condyle box 14 is schematically shown in FIG. 4 when viewed aslant from a left front and upper side.

The sagittal condylar path inclination plate 22 is aslant relative to an occlusal plane Po (at a rotational angle of the condyle member 18 about the axis A). When the condylar sphere 13 relatively moves from F to G along a slope of the sagittal condylar path inclination plate 22, F1 moves to G1 in the occlusal plane Po, and F2 moves to G2 on a sagittal surface Ps. In the case of lateral movement on a balancing side, a balancing condylar head moves from F to H. The axis C corresponds to a rotational axis of the Fischer slide. In this case, F1 moves to H1 in the occlusal plane Po, and an angle θ1 between the line (F1→G1) and the line (F1→H1) becomes a Bennett angle. On the sagittal surface Ps, F2 moves to H2. A contacting point of the condylar head moves along a deeply sinking course deviating from the straight moving path (F2→G2) along which the condylar head moves in a protrusive movement, thus to increase a gradient of the sagittal condylar path. That is, it has been known that the line (F2→H2) in the case of the lateral movement differs from the line (F2→G2) in the case of the protrusive movement. An angle θ2 difference between the line (F2→H2) and the line (F2→G2) is called a Fischer angle. Clinically, the average angle θ2 is 5 degrees.

Figure 5:
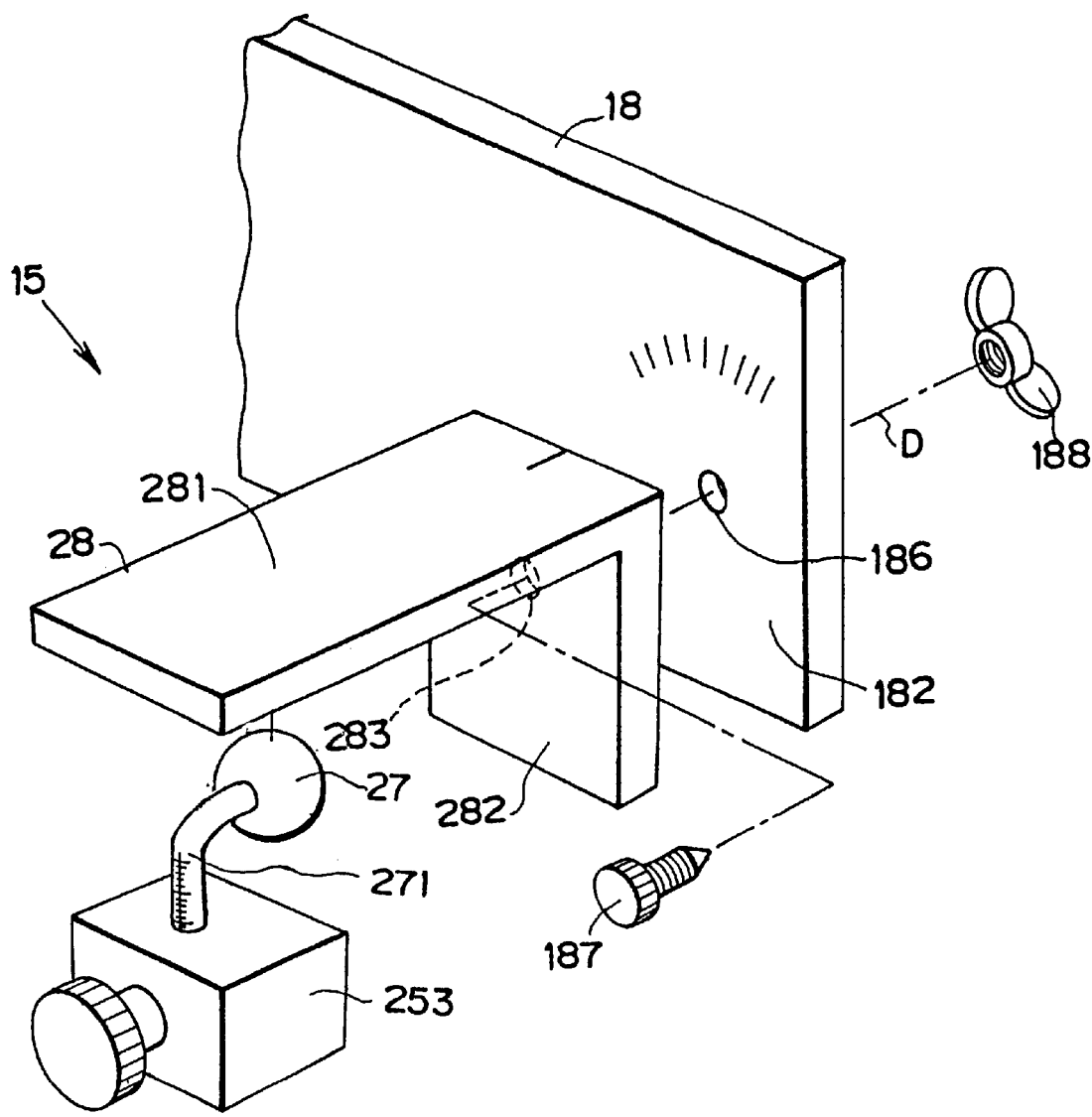
FIG. 5 is an exploded view illustrating a Bennett lift mechanism in the articulator of the invention.

Next, the Bennett lift mechanism 15 will be described with reference to FIG. 5. FIG. 5 is an exploded view showing the vicinity of the second condylar sphere 27 on a left side (right side in FIG. 2).

The Bennett lift mechanism 15 includes the second condylar sphere 27 and Bennett lift member 28 being in contact with the second condylar sphere 27. The Bennett lift member 28 is supported rotatably about an axis D by a hole 186 formed in the side panel 182 of the condyle member 18.

The Bennett lift member 28 is formed of an upper plate 281 and a side plate 282 arranged in a substantially L shape. The Bennett lift member 28 is secured rotatably about the axis D by tightening a screw 187 thrust through a hole 283 in the side panel 282 and a hole 186 in the side panel 182 of the condyle member 18, via wing nut 188. By turning the Bennett lift member 28 about the axis D, a desired Bennett lift angle can be adjusted in the same manner as the Fischer slide rotatable about the axis C as explained above with reference to FIG. 4. The side panel 182 is calibrated so as to facilitate confirmation of this angle of the Bennett lift member 28.

Each Bennett lift mechanism 15 in this embodiment is formed of the second condylar sphere 27 and the Bennett lift member 28, but may be deemed as a second condyle box 16 for regulating movement relative to the second condylar sphere 27 because the second condylar sphere 27 and Bennett lift member 28 are analogous to the condylar sphere 13 and condyle box 14.

The function of the Bennett lift mechanism 15 will be described with reference to FIGS. 6, 7A, 7B, 8A and 8B. FIG. 7A shows a model for explaining operation of the condylar sphere 13 and the second condylar sphere 27 on a working side Sw, and FIG. 7B shows a model for explaining operation of the condylar sphere 13 and the second condylar sphere 27 on a balancing side Sb.

Figure 7A:
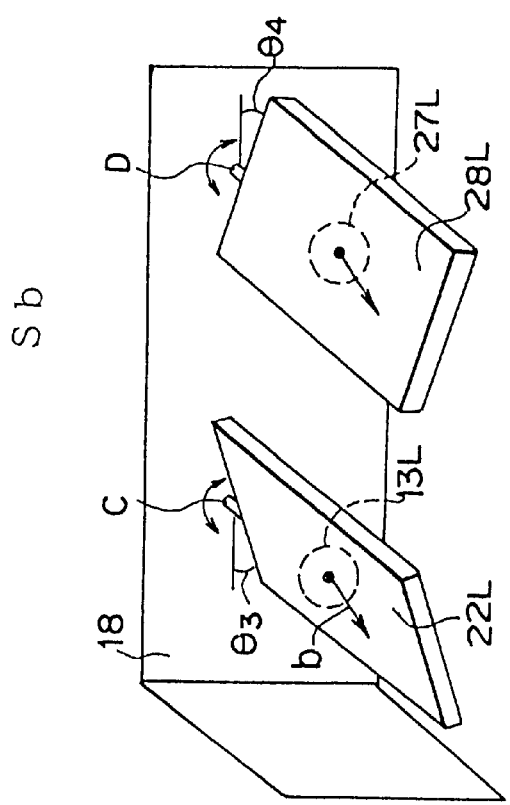
FIGS. 7A and 7B are explanatory diagrams showing operation of a Bennett lift mechanism on a working side in the articulator of the invention.
Figure 7B:
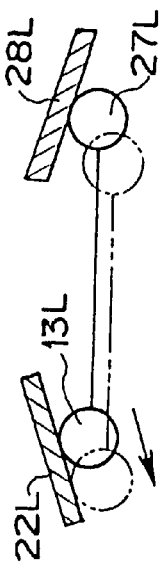
Figure 8A:
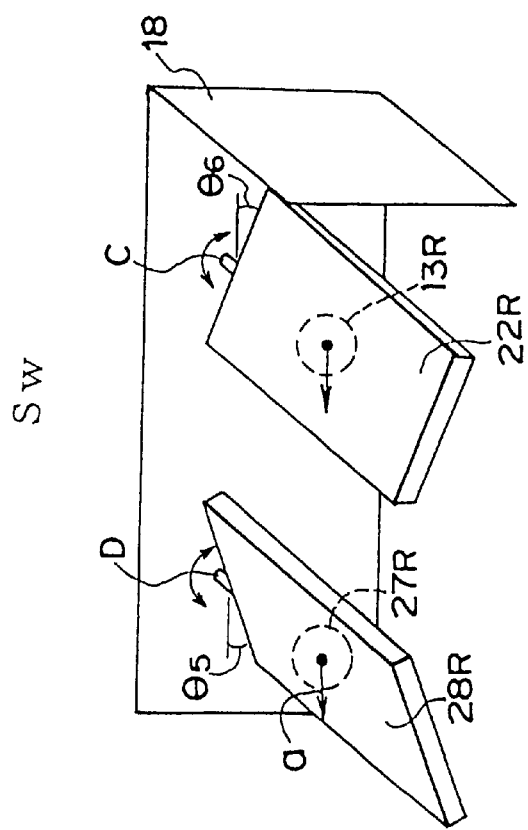
FIGS. 8A and 8B are explanatory diagrams showing operation of a Bennett lift mechanism on a balancing side in the articulator of the invention.
Figure 8B:
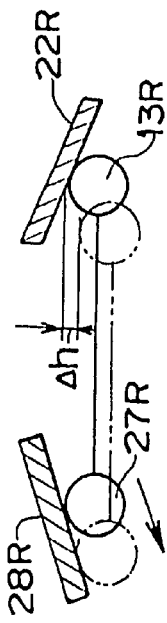
Figure 9:
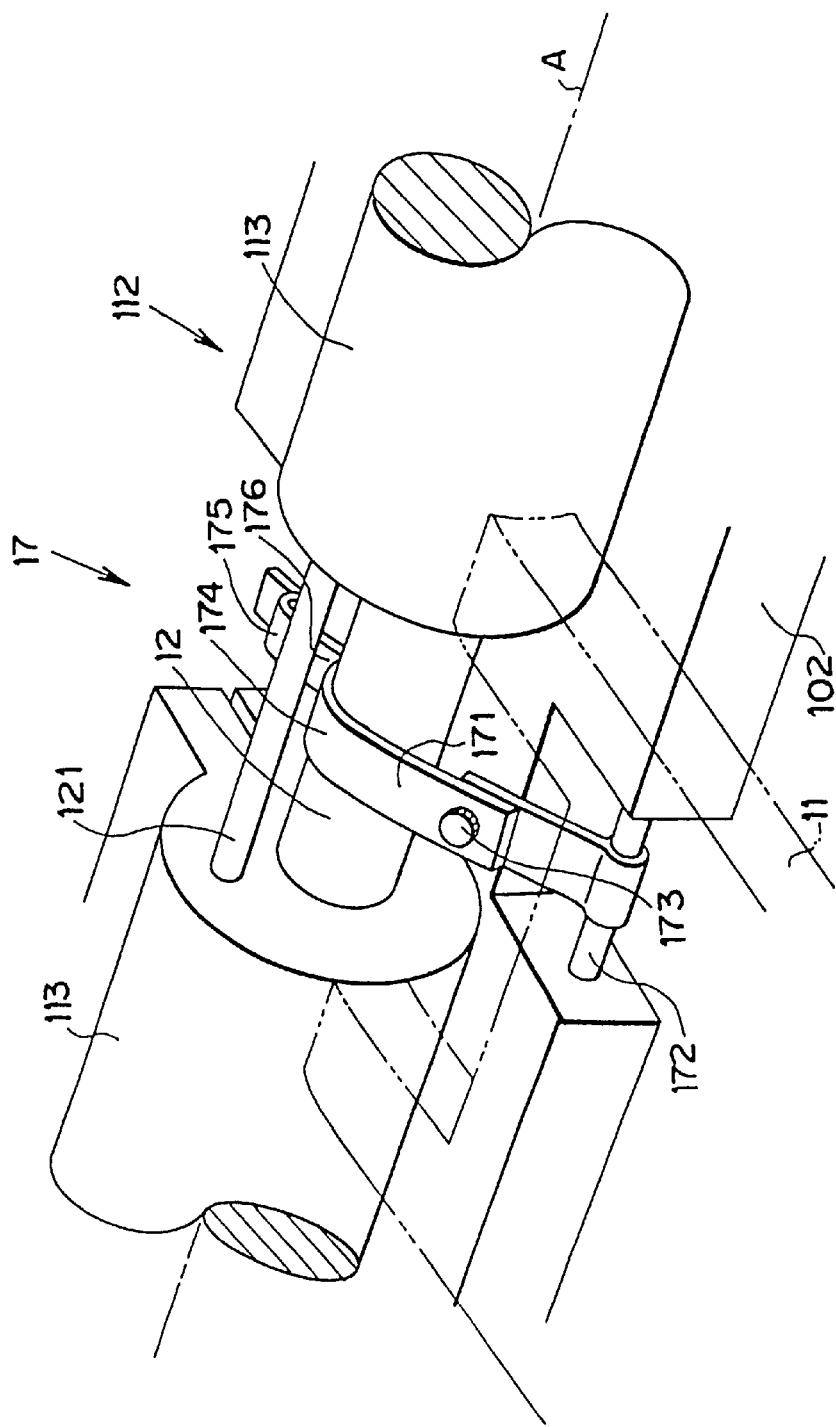
FIG. 9 is a perspective view schematically illustrating an axis fixing mechanism in the articulator of the invention.

In FIG. 7A and FIG. 8A, there are shown right and left sagittal condylar path inclination plates 22R and 22L, and right and left Bennett lift members 28R and 28L. FIG. 7B and FIG. 8B show, in section, respective movements of right and left condylar spheres 13R and 13L, and the right and left second condylar spheres 27R and 27L correspondingly to FIG. 7A and FIG. 8A. These figures illustrate a state in which the right condylar sphere 13R (corresponding to the left part in FIG. 2) works as the working part. For convenience of description, the condylar sphere moves in the illustrated embodiment, but what moves toward an opposite side along the regulation plates is the maxillar frame 11 in practice in the articulator 1 of the invention.

Figure 6:
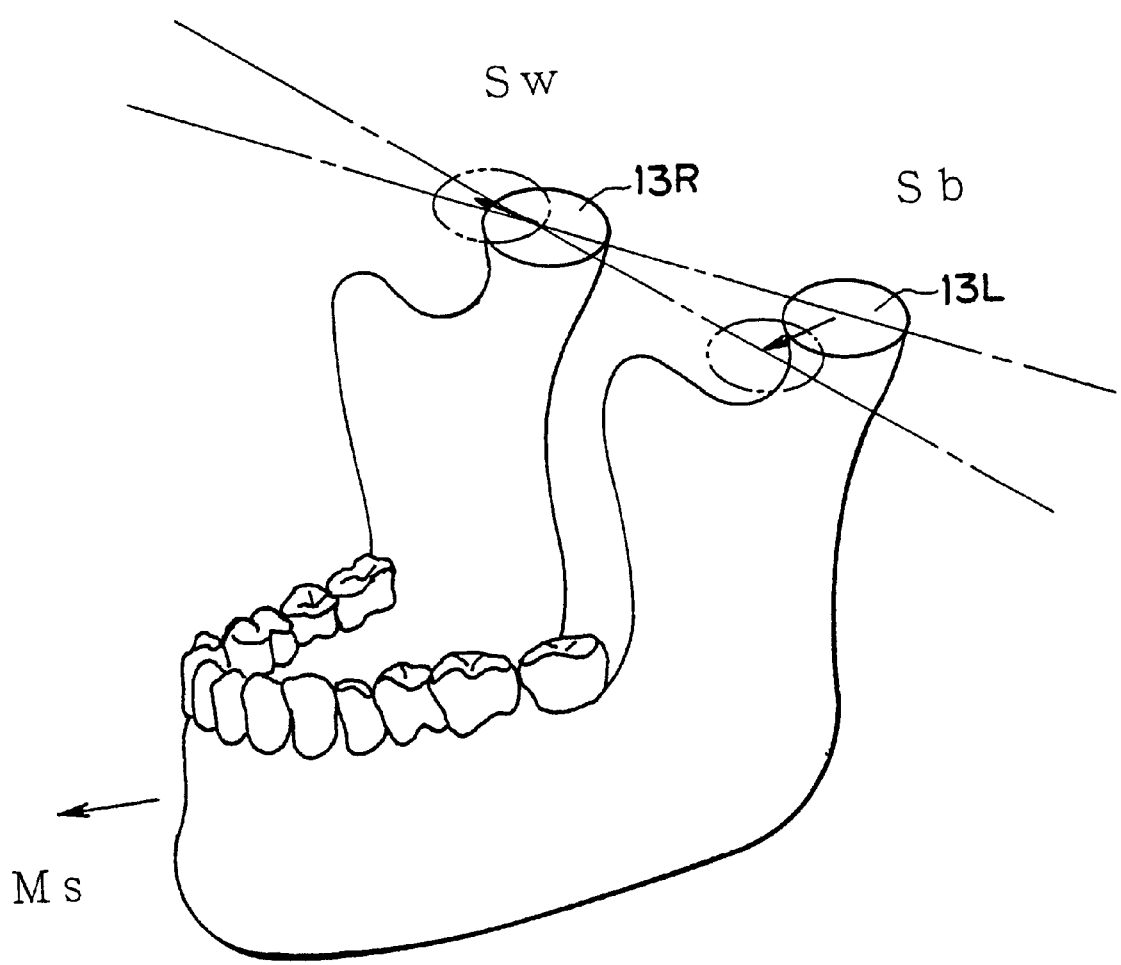
FIG. 6 is an explanatory diagram showing movement of a mandibular cast during lateral movement of the articulator of the invention.

As shown in FIG. 6, the condylar head on balancing side Sb moves inwardly, downwardly and protrusively with the lateral movement Ms, and simultaneously, the condylar head on the working side Sw moves outwardly relative to a sagittal plane. Therefore, the sagittal condylar path inclination plate 22L on the balancing side Sb is previously provided with an inward and downward inclination at an angle θ3 around the axis C corresponding to the Fischer slide. The sagittal condylar path inclination plate 22R on the working side Sw as well is previously provided with an inward and downward inclination at an angle θ6 around the axis C corresponding to the Fischer slide for making it possible to operate on the balancing side.

On the other hand, the Bennett lift member 28R on the working side is previously provided with an angle θ5, at which it inclines around the axis D. Also, the Bennett lift member 28L on the working side is previously provided with an angle θ4, at which it inclines around the axis D. These angles θ3 to θ6 may be determined according to conditions of the living subject.

The condylar sphere 13L on the balancing side Sb during lateral movement moves in an inward, downward and anterior direction (direction indicated by arrow b) while being in contact with the sagittal condylar path inclination plate 22L, as shown in FIG. 8A. At this time, the second condylar sphere 27L moves inwardly, downwardly and anteriorly together with the condylar sphere 13L, thus being separated from the Bennett lift member 28L. That is, the condylar sphere 13L is not restrained by the Bennett lift member 28L.

The condylar sphere 13R on the working side during lateral movement moves in an outward direction (direction indicated by arrow a). However, since the second condylar sphere 27R moving with the condylar sphere 13R is guided outwardly along the Bennett lift member 28R, the condylar sphere 13R is separated from sagittal condylar path inclination plate 22R by Δh. Incidentally, the maxillar frame 11 on the working side floats over the condylar sphere 13 by Δh in a practical manner. Namely, the condylar sphere 13R on the working side is restrained by the Bennett lift member 28R through the second condylar sphere 27R. As a result, vertical movement of each condylar sphere 13 on the working side is restrained without a respective one of the sagittal condylar path inclination plates 22.

As described above, since the present invention makes use of the Bennett lift mechanism in addition to the Fischer slide, vertical regulation of the condylar spheres on the respective working and balancing sides during protrusive movement and lateral movement can be reproduced individually, so that efficiency of work involved in adjusting the articulator of the invention can be improved.

Furthermore, since the Bennett lift mechanism 15, independently of the condyle box 14, is arranged on the base axis A, it can be rotated about the base axis A during an opening and closing operation.

Next, the axis fixing mechanism 17 will be described with reference to FIG. 9 and FIG. 10A through FIG. 10D.

The axis fixing mechanism 17 is used for improving operational properties of movement on the side of the maxillar frame 11 when adjusting a prosthesis by opening and closing the maxillar cast 3 and mandibular cast 2.

Usually, the maxillar frame 11 is frequently subjected to opening and closing movements in a centric occlusion position of the maxillar cast 3 and mandibular cast 2 when being adjusted with the articulator. However, since the maxillar frame 11 in the articulator 1 is in mere contact with the mandibular frame 10 as shown in FIG. 1, it can readily be separated therefrom. When the maxillar frame 11 in the articulator 1 is opened while being in contact with the condylar spheres 13 and the second condylar spheres 27, it pivots on the base axis A to open. However, as the maxillar frame 11 moves freely, it possibly comes off, or slips off, easily when released from a hand. Thus, the axis fixing mechanism 17 is provided for remedying such an unstable phenomenon at a time of opening and closing movement.

The axis fixing mechanism 17 comprises an elastic engaging member 171, which is mounted rotatably on a shaft 172 on a central portion of the base 102. The engaging member 171 is formed in an undulated shape having a first convex part 174, a second convex part 175, and a concave part 176, and is easy to bend elastically. The engaging member 171 is adjustable in its length near the shaft 172 by operating a screw 173, thereby to adjust a height of the condylar spheres 13 correspondingly.

The engaging member 171 is retained to the central shaft 12 of the base 112, or the movement regulating shaft 121 according to usage of the articulator in the manner as described below. In FIG. 10A through 10D, unnecessary component parts for explanation are not illustrated for an easily understandable manner.

First, the maxillar frame 11 is mounted on the mandibular frame 10 at the centric occlusion position, to place the central shaft 12 on the base axis A.

Figure 10A:
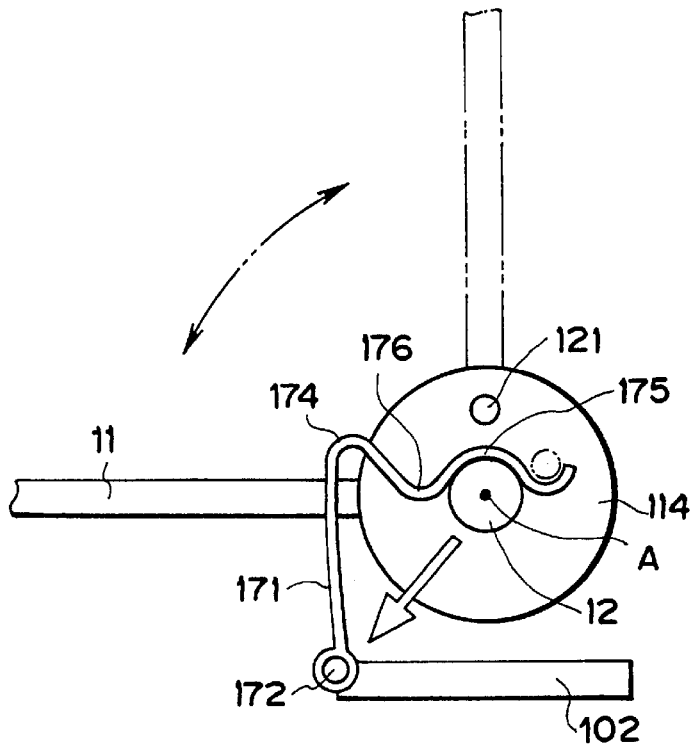
FIG. 10A through FIG. 10D show a sequence of operations of the axis fixing mechanism in the articulator of the invention.

Subsequently, in a case of moving the maxillar frame 11 in lateral and anteroposterior directions, the second convex part 175 of the engaging member 171 is hooked over the central shaft 12 as shown in FIG. 10A. At this time, the engaging member 171 showing a moderate resilient contracting force serves to adjust an occlusion of a prosthesis without clipping movement of the maxillar frame 11. Besides, the movement regulating shaft 121 is fitted into a dent of a terminal portion of the engaging member beyond the second convex part 175, thus to restrain opening of the articulator.

Figure 10B:
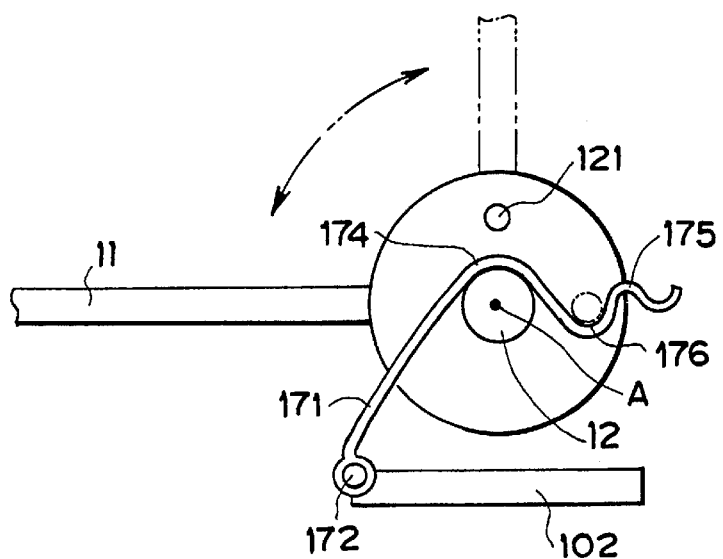

Next, in a case of performing work for restraining the maxillar frame 11 only to opening and closing movement in the course of adjusting the occlusion, as shown in FIG. 10B, the engaging member 171 is thrust one step (in the right direction in FIG. 10B) to hook the first convex part 174 onto the central shaft 12. Upon adjusting a length of the shaft by the screw 173, distance from the terminal portion of the shaft 172 of the engaging member 171 to the first convex part 174 is fixed in spite of elastic deformation of the engaging member 171, and the central shaft 12 is retained in position within the first convex part 174. Accordingly, the maxillar frame 11, when opening, is not only prevented from floating, but also rotates alone about the central shaft 12, i.e. base axis A.

When the maxillar frame 11 further rotates, the movement regulating shaft 121 falls into the concave part 176, thereby to stop rotation of the maxillar frame at a position in which a fitting state of the engaging member 171 is in proper equilibrium. As a result, reliability and reproducibility of the opening and closing movement can be improved.

Figure 10C:
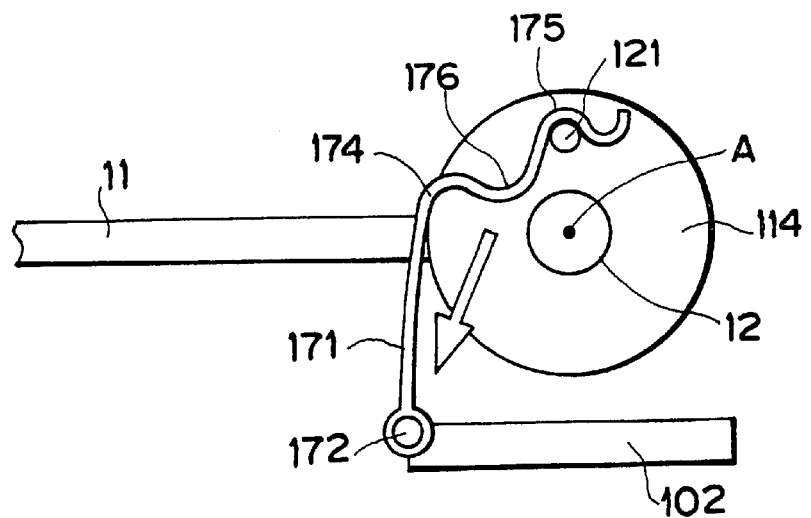

Next, usage of the articulator having the engaging member 171 hooked onto the movement regulating shaft 121 will be described. In a case of, for instance, discontinuing working for adjusting the occlusion, the engaging member 171 is elongated to hook the second convex part 175 onto the movement regulating shaft 121 as shown in FIG. 10C. In this case, as a relatively strong pushing-down force is exerted on the maxillar frame 11 by a resilient contracting force of the engaging member 171, the maxillar frame 11 is not easily opened even if it experiences a shock imprudently, consequently to prevent dislocation of the maxillar and mandibular casts.

Figure 10D:
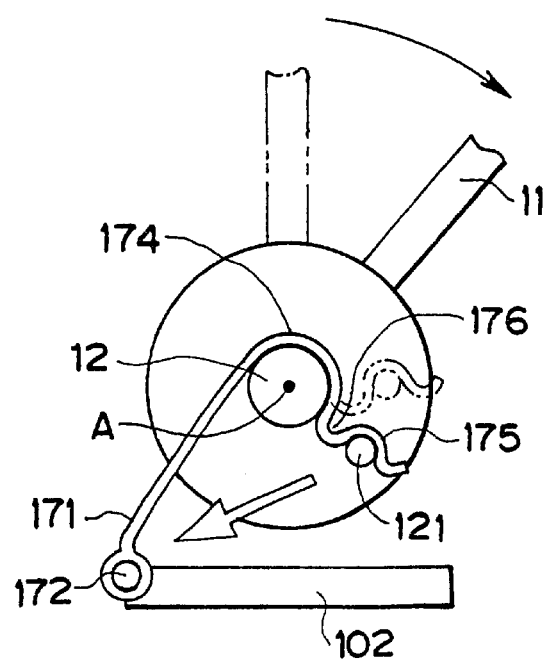

When the maxillar frame 11 is opened against the resilient contracting force of the engaging member 171, the first convex part 174 is hooked onto the central shaft 12 in a state of hooking the movement regulating shaft 121 on the second convex part 175. Upon surmounting a barrier, the engaging member 171 imparts its resilient contracting force onto the central shaft 12 to maintain the maxillar frame 11 in its open state, as shown in FIG. 10D. Consequently the maxillar frame 11 assumes its stable state in which it is hard to close. In this state, even if the articulator experiences a shock imprudently, the maxillar and mandibular casts can be prevented from being damaged due to an abrupt closing operation of the maxillar frame.

As noted above, the engaging member 171 carries out a function of preventing dislocation of the central shaft serving as a rotational center, during the opening and closing movement around the base axis A. A variation of a manner of retaining the maxillar and mandibular casts in position with the engaging member, according to usage of the articulator, makes it possible to improve efficiency of work for handling the articulator and prevents an unexpected accident.

Incidentally, the axis fixing mechanism 17 in the first embodiment is illustrated as one example, and should not be understood as being limited to the structured as illustrated. Any mechanism capable of maintaining the central shaft in a fixed position when performing the opening and closing movement of the maxillar frame 11 may be substituted therefor, or more simple structure for merely catching a hook-shaped member onto the central shaft may be used in place of the aforementioned engaging member.

The operation of the articulator 1 having the structure described above will be explained hereinafter.

First, a gauge for each regulation plate is initially set, e.g. with the sagittal condylar path inclination plate at 0 degrees, Fischer slide at 0 degrees, Bennett angle at 30 degrees, rear angle at 30 degrees, and Bennett lift angle at 20 degrees. The maxillar cast 3 mounted on a mounting plate by use of gypsum is fixed on the maxillar frame 11. Subsequently, the mandibular cast 2 mounted on another mounting plate by use of gypsum is fixed on the mandibular frame 10. In this state, the Bennett angle regulation plate 21 and the sagittal condylar path inclination plate 22 of each condyle box 14, and rear wall 23 are in contact with a corresponding one of the condylar spheres 13, and the Bennett lift member 28 of each Bennett lift mechanism 15 is in contact with a corresponding one of the second condylar spheres 27. At this time, a height of the respective right and left condylar spheres 13 coming into contact with these components, and an interval between the right and left condylar spheres 13 are regulated.

A checkbite taking of a positional relation (occlusion) of upper and lower teeth of a living subject, which has been prepared by ultimately checking lateral and anteroposterior movements of the teeth, is extracted from the living subject by use of gypsum, resin or the like. Then, the maxillar cast is placed on the mandibular cast across the checkbite thus prepared. At this time, each regulation plate is separated from the condylar spheres 13 and the second condylar spheres 27 (separation is indispensable). Thereupon, each regulation plate is adjusted in the following sequence, to reproduce a condition after movement.

1) Vertical regulation of the right and left condylar spheres during protrusive movement:

The condyle member 18 is turned about the axis A, to be fixed at an angle after the movement. Consequently, a protrusive sagittal condylar path inclination of the sagittal condylar path inclination plate 22 is adjusted.

2) Vertical regulation of the condylar sphere on the balancing side during lateral movement:

Upon loosening the wing nut 185, the support member 19 is turned about the axis C, to be fixed at the angle after the movement. Consequently the sagittal condylar path inclination plate 22 is set at the Fischer angle.

3) Lateral regulation of the condylar sphere on the balancing side during lateral movement:

Upon loosening the wing nut 196, the Bennett angle regulation plate 21 is turned about the axis B, to be fixed at an angle after the movement. Consequently, the Bennett angle of the Bennett angle regulation plate 21 is adjusted.

4) Anteroposterior regulation of the condylar sphere on the working side during lateral movement:

Upon loosening the wing nut 198, the rear wall 23 is turned about the axis B, to be fixed at an angle after the movement. Consequently, a rear wall angle of the rear wall is adjusted.

5) Vertical regulation of the second condylar sphere on the working side during lateral movement:

Upon loosening the wing nut 188, the Bennett lift member 28 is turned about the axis D, to be fixed at an angle after the movement. Consequently, the Bennett lift angle of the Bennett lift mechanism 15 is adjusted.

Next, on the basis of an occlusal condition of the maxillar cast 3 and mandibular cast 2 in the centric occlusion before the movement, the maxillar frame 11 is shifted along the adjusted regulation plates in the anteroposterior and lateral directions, to reproduce the respective movements. The relative movements on the side of the maxillar frame 11 can be reproduced by moving the portion to the side opposite to the intended direction.

Reproduction of the protrusive movement is fulfilled by relatively moving the right and left condylar spheres 13 along the right and left sagittal condylar path inclination plates 22 in their contacting state.

Reproduction of the lateral movement on the balancing side is fulfilled by relatively moving the condylar spheres 13 along the sagittal condylar path inclination plates 22 and the Bennett angle regulation plates 21 in their contacting state. Reproduction of the lateral movement on the working side is fulfilled by allowing the Bennett lift mechanism 15 to move relative to the second condylar sphere 27 along the Bennett lift member 28 in its contacting state. Consequently, the sagittal condylar path inclination plate 22 on the working side is separated from the condylar sphere 13 and rises, to perform the Bennett lift movement. At this time, the rear wall 23 on the working side comes into contact with the condylar sphere 13 to regulate movement in the anteroposterior direction.

Upon completion of all of the adjustments, the rear angle is set in the sagittal direction, and then, the condylar sphere 13 is subjected to posterior movement to effect posterior adjustment. The sagittal condylar path inclination may be provided as required.

As described, the articulator 1 of the invention fulfills a respective adjustments independently without hindering a preceding adjustment by a succeeding adjustment.

Figure 11:
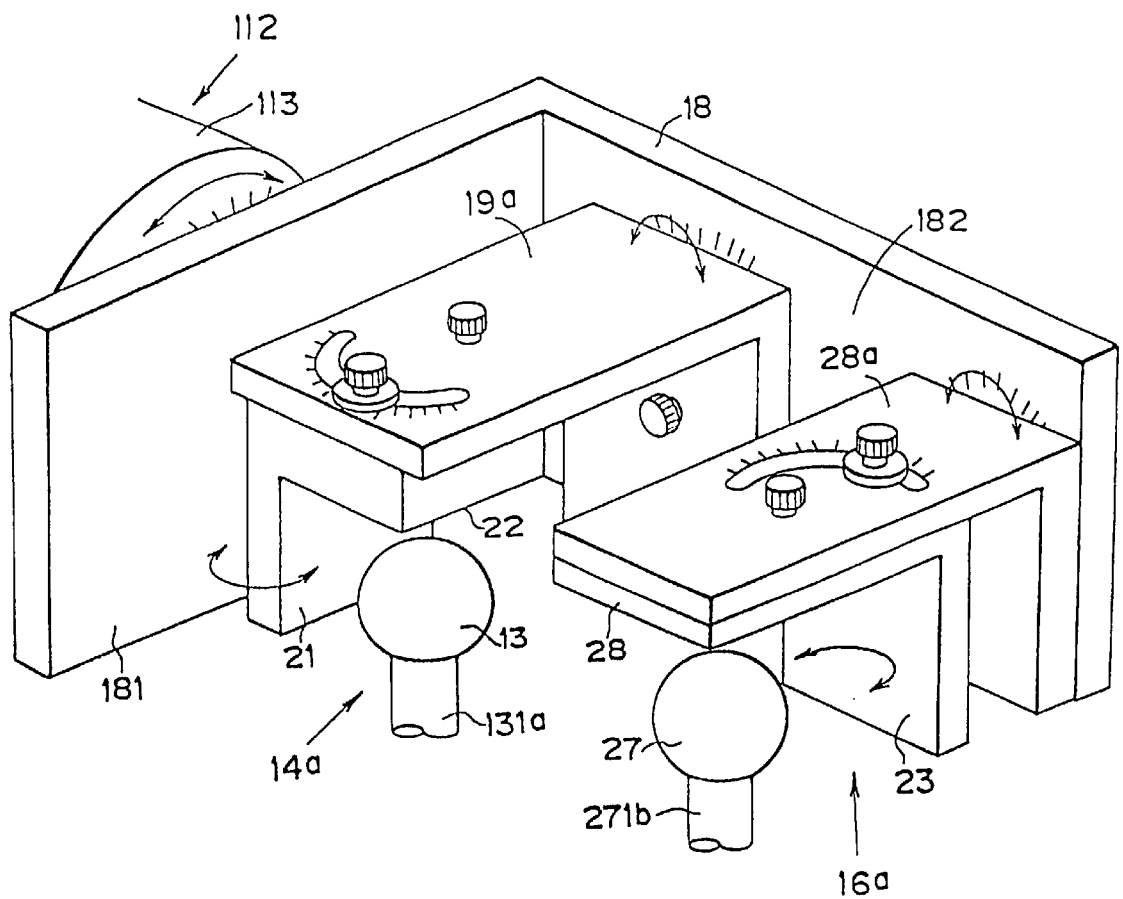
FIG. 11 is a perspective view schematically illustrating a periphery of a left condylar sphere in a second embodiment of the articulator according to the invention.

Next, a second embodiment of the articulator according to the present invention will be described with reference to FIG. 11. The articulator in this embodiment has anteroposterior regulation plates independent of a condyle box. FIG. 11 illustrates a circumference of a left condylar sphere (right side in FIG. 1). In the diagrams, reference numerals which have equivalents in the diagrams of the embodiment mentioned above denote identical or equivalent component parts. Description of these component parts is omitted below to avoid repetition.

In the second embodiment, a condyle box 14a and a second condyle box 16a disposed on the maxillar frame 11 are mounted, respectively coming into contact with the condylar sphere 13 and the second condylar sphere 27 disposed on the base 102 (not shown in FIG. 11).

Within the condyle box 14a, there are arranged a Bennett angle regulation plate 21 and sagittal condylar path inclination plate 22, and within the second condyle box 16a, there are arranged a rear wall 23 and a Bennett lift member 28 of a Bennett lift mechanism 15.

At a position in which only the Bennett lift member 28 is disposed in the first embodiment described above, the rear wall 23 serving as the anteroposterior regulation plate is added independently of the condyle box 14, to form the second condyle box 16a in the second embodiment. By positioning the rear wall 23 independently in this manner, the first condyle box functioning as a regulation mechanism during a balancing operation, and the second condyle box functioning as a regulation mechanism during a working operation, serve to definitely separate the balancing operation and the working operation and prevent interference of the regulation plates with the condylar sphere 13, and consequently to enlarge a movable range in adjusting the rear wall angle.

Further, the Bennett angle regulation plate 21 of the condyle box 14a may be mounted independently on the condyle box 16a. In this case, the movable range for lateral regulation can be enlarged.

By arbitrarily separating the respective regulation plates from each other in the condyle box 14a and the second condyle box 16a as noted above, interference of the regulation plates with each other can be restricted. Although the sagittal condylar path inclination plate 22 and the Bennett lift member 28 must be disposed separately in principle, there may be assembled the Bennett lift member 28 in the condyle box 14a and the sagittal condylar path inclination plate 22 in the second condyle box 16a.

Figure 12:
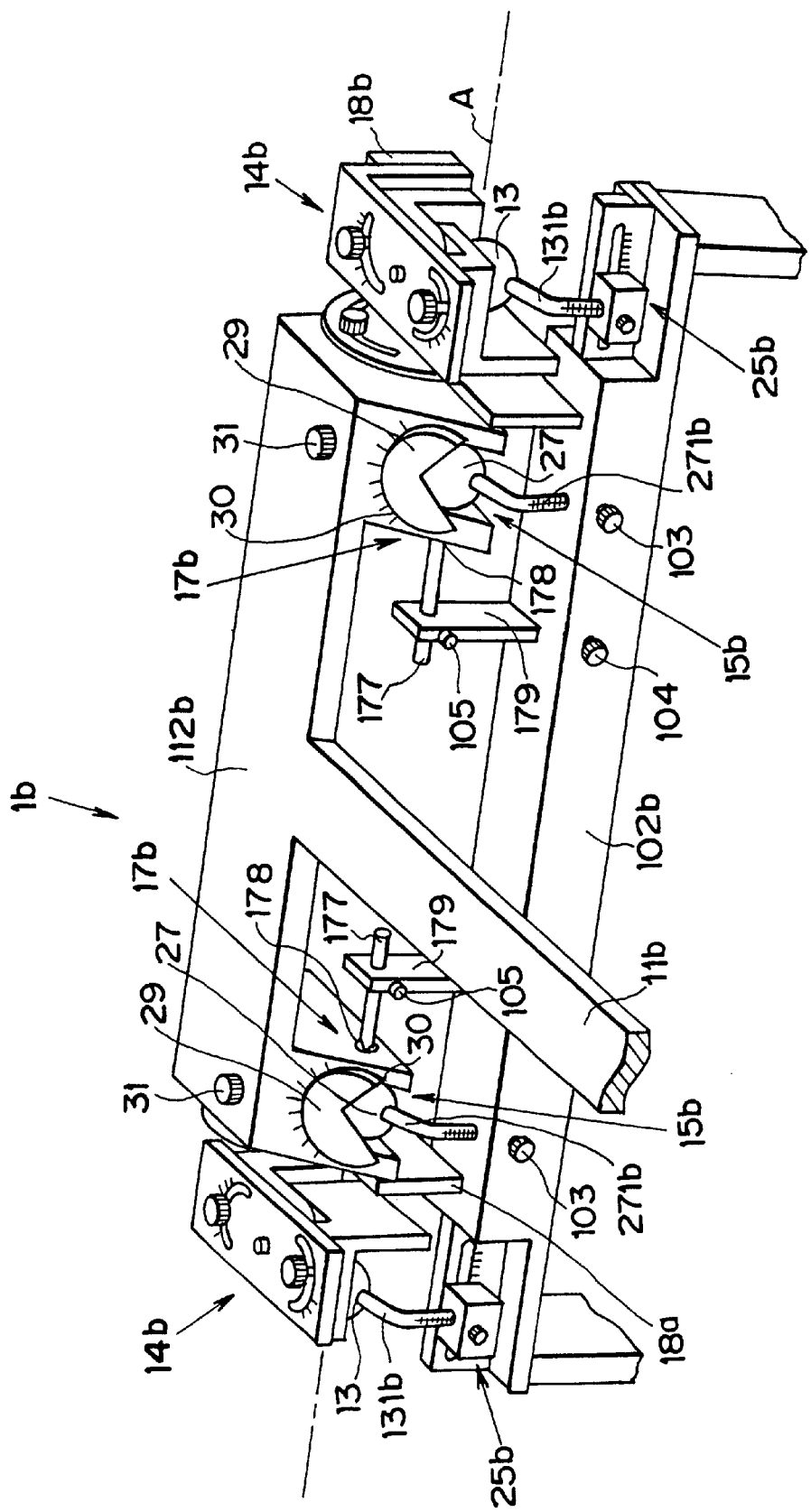
FIG. 12 is a perspective view illustrating in part a third embodiment of the articulator according to the invention.
Figure 13:
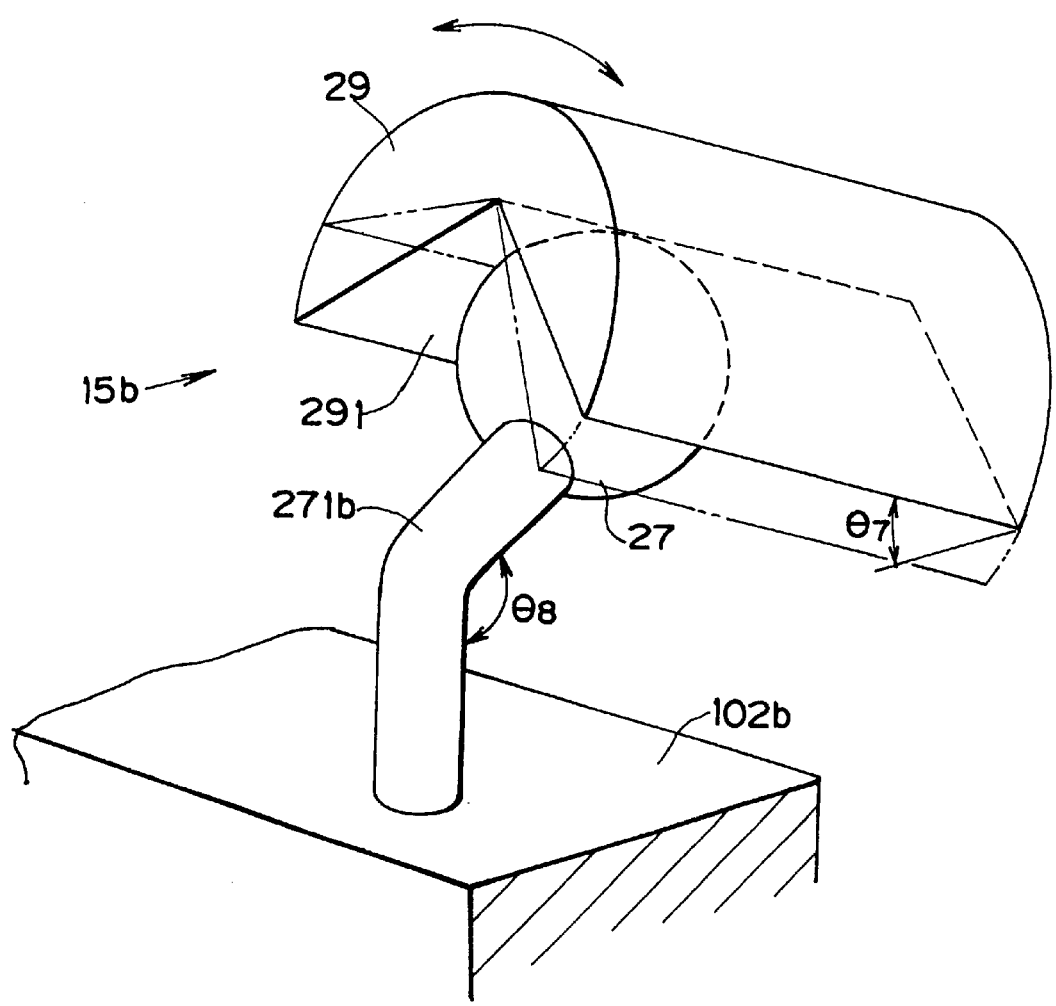
FIG. 13 is an explanatory diagram showing a Bennett lift mechanism in the articulator of FIG. 12.
Figure 14:
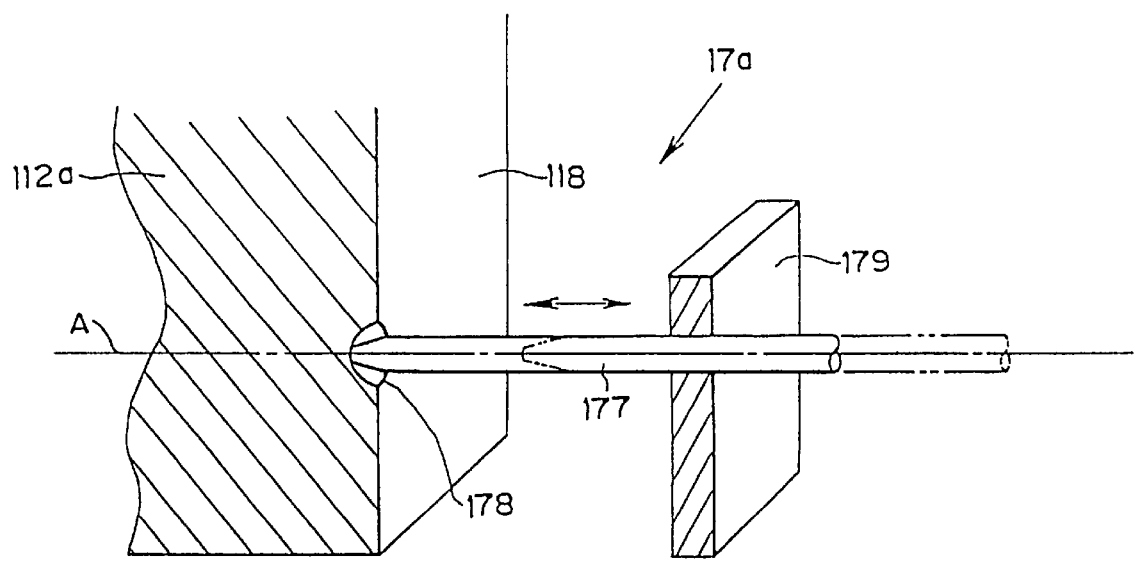
FIG. 14 is a sectional view illustrating an axis fixing mechanism in the articulator of FIG. 12.
Figure 15:
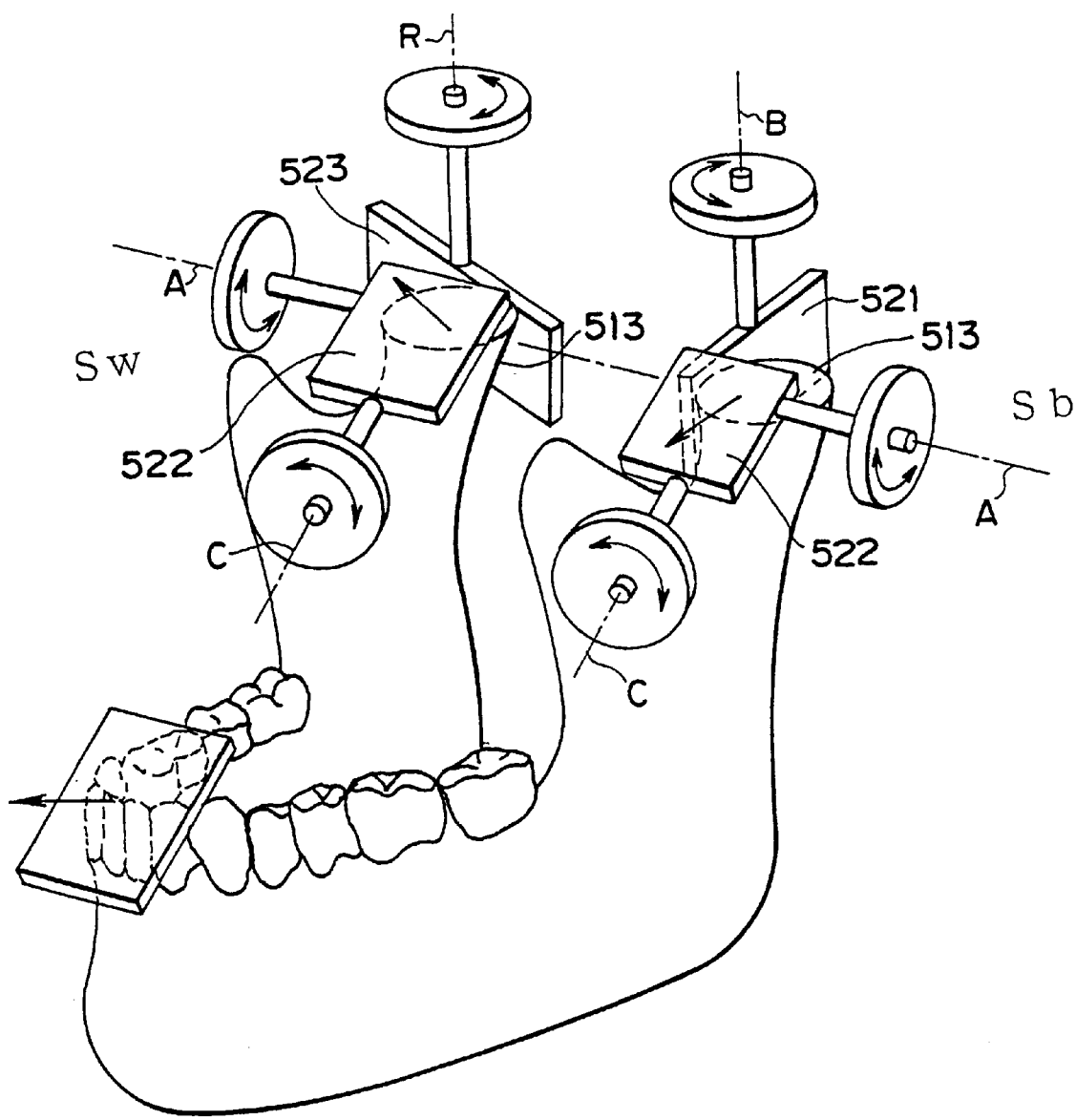
FIG. 15 is an explanatory diagram showing a regulating mechanism in a prior art articulator.
Figure 16:
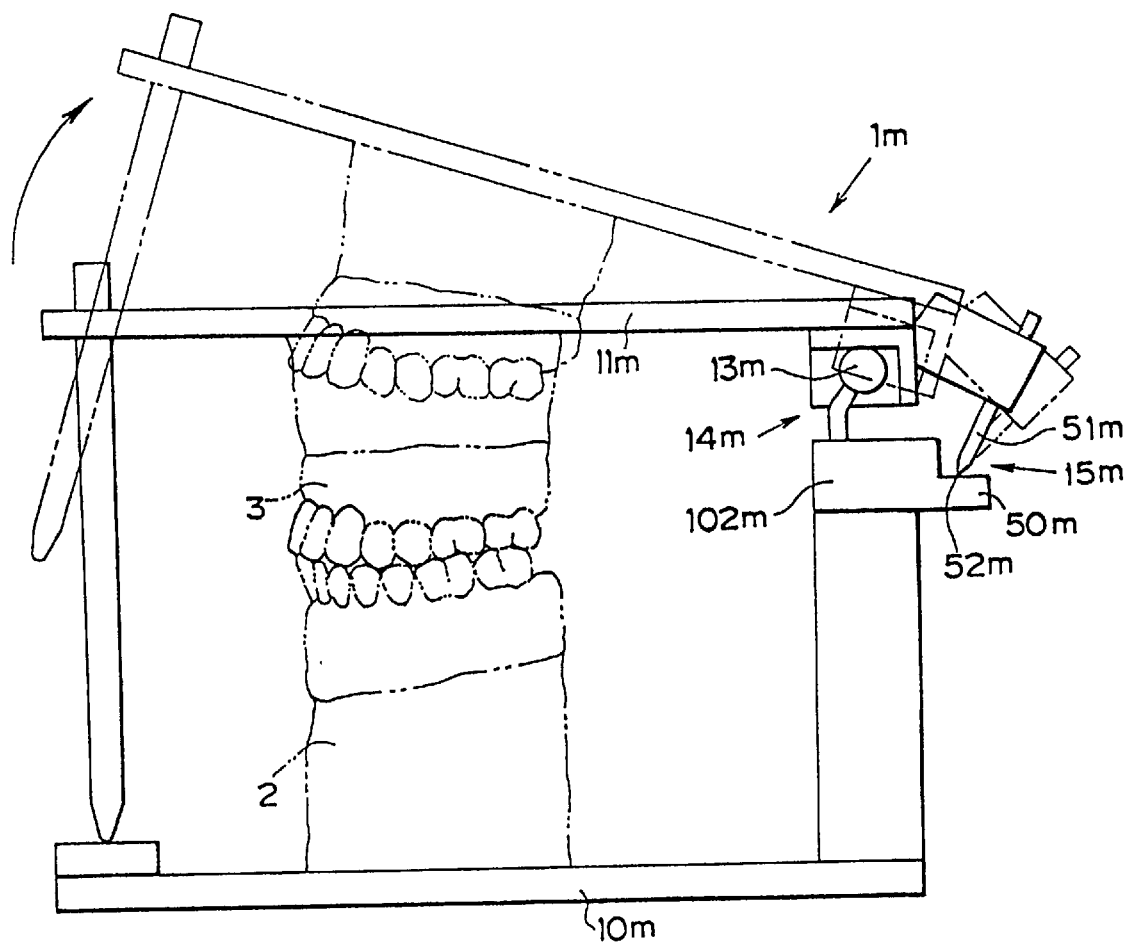
FIG. 16 is a schematic sectional view illustrating movement of the prior art articulator.

Next, a third embodiment of the articulator according to the present invention will be described with reference to FIG. 12 through FIG. 14. The third embodiment is different from the first embodiment with respect to the Bennett lift mechanism. In this illustrated embodiment, reference numerals, which have equivalents in the diagrams of the foregoing embodiments mentioned above denote identical or equivalent component parts. Description of these component parts is omitted below to avoid repetition. FIG. 12 is a perspective view illustrating in part the articulator of the third embodiment. FIG. 13 is an explanatory diagram showing the Bennett lift mechanism, and FIG. 14 is a sectional view illustrating an axis fixing mechanism of the third embodiment.

On a base 102b of a mandibular frame, there are mounted a pair of condylar spheres 13, and a pair of second condylar spheres 27 inside the condylar spheres 13. These condylar spheres are placed on base axis A. The condylar spheres 13 can be adjusted in height and interval by virtue of an intercondylar adjusting mechanism 25b. Each second sphere 27 is adjustable in height in accordance with a respective condylar sphere 13 by virtue of a screw 103.

On either end of a base 112b of a maxillar frame 11b, a condyle box 14b is disposed rotatably through a condyle member 18b and comes in contact with the condylar sphere 13. Bennett lift mechanisms 15b are mounted in pairs on the base 112b inside the condyle boxes 14b and come into contact with the second condylar spheres 27.

Each Bennett lift mechanism 15b has a Bennett angle regulation plate 29 in contact with a corresponding one of the second condylar spheres 27. The Bennett angle regulation plate 29 is of a columnar shape having a notch 291, and is fitted into an insertion hole 30 formed in the base 112b. The insertion hole 30 is inclined downwardly at an angle θ7 in a depthwise direction, i.e. about 15 degrees in this embodiment, as shown in FIG. 13.

The Bennett angle regulation plate 29 is freely rotatable within the insertion hole 30 and secured by a screw 31. The notch 291 is so formed that a central axis of the Bennett angle regulation plate 29 passes through a center of the second condylar sphere 27, and the second condylar sphere 27 is positioned between and comes into contact with two slopes constituting the notch 291.

The Bennett angle regulation plate 29 is shifted by being rotated relative to the insertion hole 30, so that angles of the slopes of the notch 291 coming into contact with the second condylar sphere 27 can vary to adjust the Bennett lift angle. By calibrating a periphery of the insertion hole 30, rotational position of the Bennett angle regulation plate 29 can easily be confirmed.

Operation of the Bennett lift mechanism 15b in the third embodiment will be explained.

An outer one of the two slopes constituting the notch 291 in this embodiment corresponds to the Bennett lift plate 28 in the first embodiment. Thus, by turning the Bennett angle regulation plate 29 within the insertion hole 30, the same function as that in the case in which the Bennett lift plate 28 is inclined can be obtained. Accordingly, in the case of performing lateral movement as shown in FIG. 6, vertical regulation is carried out in such a manner that the condylar sphere 13 on the working side is separated from the sagittal condylar path inclination plate 22 and the second condylar sphere 27 is guided by the Bennett angle regulation plate 29.

The arrangement in which the Bennett angle regulation plate 29 is inserted into the insertion hole 30 inclined downwardly at the angle θ7 in the depthwise direction is provided for the purpose of hindering movement of the Bennett angle regulation plate relative to the second condylar sphere 27 on the balancing side in a condition of sagittal condylar path inclination of 0 to −15 degrees during protrusive movement.

As noted above, the Bennett lift mechanism 15b in the third embodiment performs vertical regulation of the condylar sphere on the working side. As a result, an articulator capable of completely reproducing movement of the mandible can be obtained.

An axis fixing mechanism 17b in the third embodiment will be described hereinafter.

Since an axial shaft 177 disposed on the base 102b is hooked onto an engaging portion 178, the axis fixing mechanism 17b rotates about the base axis A at a time of opening and closing movement. The axial shaft 177 penetrates through support wall 179 projecting from the base 102b, so that protrusion of the shaft 177 from the support wall can be adjusted in length via a screw 105. The support wall 179 is adjustable in height via a screw 104, so that the axial shaft 177 can always be placed on the base axis A even if height of the condylar sphere 13 is changed.

The engaging portion 178 is formed in an end surface 118 on an inside porton of the base 112b, and is positioned on the base axis A in light of the positional relationship between itself and the Bennett angle regulation plate 29. The engaging portion 178 has a suitable shape for receiving a leading end of the axial shaft 177; that is, a substantially hemispherical shape is desirable.

When the maxillar frame 11b moves along the regulation plates to adjust occlusion, the axial shaft 177 is placed so as not to come into contact with the engaging portion 178.

When performing the opening and closing movement, the axial shaft 177 is thrust into the engaging portion 178 and secured rotatably. At this time, the maxillar frame 11b makes the opening and closing movement around the base axis A similarly to how the maxillar frame 11 makes the opening and closing movement in the first embodiment described above, and is prevented from separating from the mandibular frame. As a result, the opening and closing movement of maxillar and mandibular casts can be stably performed without deviation from the rotational axis, to thus improve efficiency of operation for adjusting a prosthesis.

Upon completion of the opening and closing movement of the maxillar and mandibular casts, when the articulator is again activated by moving the maxillar frame 11b, the axis fixing mechanism 17b can easily be demounted merely by separating the axial shaft 173.

Thus, according to the articulator of the invention with the axis fixing mechanism 17b having its rotational center held in place on the base axis A, the desired closing and opening movement of the maxillar and mandibular casts can be performed invariably at the same position even if repeated many times, so that occlusal conditions can be completely reproduced at an identical centric occlusion position.

Axial shaft 131b of the condylar sphere 13 and axial shaft 271b of the second condylar sphere 27 are inclined at an angle θ8 in a depthwise direction. In the embodiment of FIG. 13, the angle θ8 is on the order of 45 degrees. This angle is determined taking into consideration the fact that movement of the maxillar frame 11b is impeded at the time of the opening and closing movement, but the angle and structure thereof should not be limited thereto.

It is needless to say that all the mechanisms and components in the foregoing embodiments may be used in their modified form or in combination according to usage of the articulator. For instance, the structure in which the condylar sphere 13 and second condylar sphere 27 are in contact with the condyle box and Bennett lift as in the third embodiment may be applied to the first embodiment. Or, the axis fixing mechanism 17 in the first embodiment may be applied to the third embodiment. Thus, the components in each embodiment may be variously combined and applied to other embodiments in various ways.

As is described above in detail, a completely reproducible articulator according to the present invention has a characteristic structure wherein the Bennett lift mechanism is provided independently of the condyle box and disposed on the base axis connecting the paired condylar spheres. Accordingly, vertical regulation of movements of the mandible in the lateral (rightward and leftward) and anteroposterior directions can be individually reproduced, and further, the opening and closing movement around the base axis can be performed in the centric occlusion position. Thus, the articulator of the invention remarkably excels in efficiency of operating the regulation plates, and reproducibility of mandibular movement.

Furthermore, the articulator of the invention can securely maintain with ease a rotational center on the base axis by virtue of the axis fixing mechanism to perform the opening and closing movement, consequently to improve efficiency of operating the articulator at the time of the opening and closing movement.

Besides, since the central shaft of the articulator of the invention is secured without causing deviation from the base axis, the reproducibility of an occlusion in the articulator is enhanced. Moreover, since each regulation plate in the articulator of the invention is mounted independently of the condyle box, restraint in the movable region of the regulation plates due to interference of the regulation plates with each other can be effectively prevented, thus to enable the mandibular movement to be completely reproduced with fidelity on a model of the living subject.

It is to be understood that the invention is not limited in its application to the details of construction and arrangement of parts illustrated in the accompanying drawings, since the invention is capable of other embodiments and of being practiced or carried out in various ways. Also, it is to be understood that the phraseology or terminology employed herein is for the purpose of description and not of limitation.

What is claimed is:

1. A completely reproducible articulator comprising:
   a maxillar frame for supporting a maxillar cast;
   a mandibular frame for supporting a mandibular cast;
   two condylar spheres between said mandibular frame and said maxillar frame;.
   condyle boxes between said mandibular frame and said maxillar frame; and
   Bennett lift mechanisms disposed on a base axis that interconnects said two condylar spheres, with said Bennett lift mechanisms being independent of said condyle boxes.

2. The completely reproducible articulator according to claim 1, further comprising two additional condylar spheres on said base axis, wherein said two additional condylar spheres are to be restrained in vertical movement by said Bennett lift mechanisms.

3. The completely reproducible articulator according to claim 2, further comprising an axis fixing mechanism for coinciding said base axis with a rotational center of said mandibular and maxillar frames that is defined upon opening and closing said mandibular and maxillar frames while said maxillar and mandibular frames support the maxillar and mandibular casts, respectively, relative to one another at a centric occlusion position.

4. The completely reproducible articulator according to claim 3, wherein said axis fixing mechanism includes a resilient engaging member for resiliently interconnecting said mandibular frame and said maxillar frame.

5. The completely reproducible articulator according to claim 3, wherein said axis fixing mechanism includes an axial shaft disposed on said base axis between said mandibular frame and said maxillar frame, and an engaging member, wherein said engaging member is arranged to be hooked on said axial shaft during opening and closing movement of said mandibular and maxillar frames.

6. The completely reproducible articulator according to claim 1, further comprising an axis fixing mechanism for coinciding said base axis with a rotational center of said mandibular and maxillar frames that is defined upon opening and closing said mandibular and maxillar frames while said maxillar and mandibular frames support the maxillar and mandibular casts, respectively, relative to one another at a centric occlusion position.

7. The completely reproducible articulator according to claim 6, wherein said axis fixing mechanism includes a resilient engaging member for resiliently interconnecting said mandibular frame and said maxillar frame.

8. The completely reproducible articulator according to claim 6, wherein said axis fixing mechanism includes an axial shaft disposed on said base axis between said mandibular frame and said maxillar frame, and an engaging member, wherein said engaging member is arranged to be hooked on said axial shaft during opening and closing movement of said mandibular and maxillar frames.

9. The completely reproducible articulator according to claim 1, further comprising anteroposterior regulations plates for regulating said two condylar spheres on a working side to move in an anteroposterior direction.

10. The completely reproducible articulator according to claim 1, further comprising mesio-lateral regulation plates for regulating said two condylar spheres on a balancing side to move in a mesio-lateral direction.

11. The completely reproducible articulator according to claim 1, further comprising:
   two additional condylar spheres between said mandibular frame and said maxillar frame, with said two additional condylar spheres and said two condylar spheres being co-axial with one another; and
   two additional lift mechanisms,
   wherein said two additional condylar spheres are associated with said Bennett lift mechanisms, respectively, and said two condylar spheres are associated with said two additional lift mechanisms, respectively.

12. The completely reproducible articulator according to claim 11, wherein each of said Bennett lift mechanisms includes an upper plate positioned above and in contact with a respective one of said two additional condylar spheres, and each of said two additional lift mechanisms includes an upper plate positioned above and in contact with a respective one of said two condylar spheres.

13. The completely reproducible articulator according to claim 12, wherein said upper plates of said Bennett lift mechanisms and said upper plates of said two additional lift mechanisms are rotatable about parallel first axes, respectively.

14. The completely reproducible articulator according to claim 13, wherein said Bennett lift mechanisms and said two additional lift mechanisms further include screws to set rotational positions of said upper plates about said first axes, respectively.

15. The completely reproducible articulator according to claim 14, wherein each of said condyle boxes includes a first plate rotatable about a second axis that is orthogonal to said first axes, and a second plate rotatable about said second axis, with said first and second-plates being rotatable about said second axis such that said first and second plates can be arranged generally orthogonally relative to one another, and with each of said two condylar spheres being positioned between respective said first and second plates.

16. The completely reproducible articulator according to claim 15, comprising a first screw to set a rotational position of said first plate about said second axis, and a second screw to set a rotational position of said second plate about said second axis.

17. The completely reproducible articulator according to claim 15, wherein said first plate corresponds to an antero-posterior regulation plate for regulating one of said two condylar spheres on a working side to move in an antero-posterior direction, and said second plate corresponds to a mesio-lateral regulation plate for regulating one of said two condylar spheres on a balancing side to move in a mesio-lateral direction.

18. The completely reproducible articulator according to claim 11, further comprising an axis fixing mechanism for coinciding said base axis with a rotational center of said mandibular and maxillar frames that is defined upon opening and closing said mandibular and maxillar frames while said maxillar and mandibular frames support the maxillar and mandibular casts, respectively, relative to one another at a centric occlusion position.

19. The completely reproducible articulator according to claim 18, wherein said axis fixing mechanism includes a resilient engaging member for resiliently interconnecting said mandibular frame and said maxillar frame.

20. The completely reproducible articulator according to claim 18, wherein said axis fixing mechanism includes an axial shaft disposed on said base axis between said mandibular frame and said maxillar frame, and an engaging member, wherein said engaging member is arranged to be hooked on said axial shaft during opening and closing movement of said mandibular and maxillar frames.

* * * * *